US012038439B2

(12) United States Patent
Daaboul et al.

(10) Patent No.: US 12,038,439 B2
(45) Date of Patent: Jul. 16, 2024

(54) DETECTION OF EXOSOMES HAVING SURFACE MARKERS

(71) Applicant: Unchained Labs, Pleasanton, CA (US)

(72) Inventors: George Daaboul, Watertown, MA (US); David S. Freedman, Newton Highlands, MA (US)

(73) Assignee: UNCHAINED LABS, Pleasanton, CA (US)

( * ) Notice: Subject to any disclaimer, the term of this patent is extended or adjusted under 35 U.S.C. 154(b) by 0 days.

(21) Appl. No.: 17/579,313

(22) Filed: Jan. 19, 2022

(65) Prior Publication Data

US 2022/0137055 A1 May 5, 2022

Related U.S. Application Data

(62) Division of application No. 16/074,259, filed as application No. PCT/US2017/016434 on Feb. 3, 2017, now Pat. No. 11,262,359.

(60) Provisional application No. 62/291,848, filed on Feb. 5, 2016.

(51) Int. Cl.
*G01N 21/47* (2006.01)
*G01N 21/25* (2006.01)
*G01N 21/45* (2006.01)
*G01N 21/77* (2006.01)
(Continued)

(52) U.S. Cl.
CPC ..... *G01N 33/57438* (2013.01); *G01N 21/253* (2013.01); *G01N 21/45* (2013.01); *G01N 21/47* (2013.01); *G01N 21/7703* (2013.01); *G01N 33/54373* (2013.01); *G01N 2021/7773* (2013.01); *G01N 2201/062* (2013.01); *G01N 2400/40* (2013.01)

(58) Field of Classification Search
None
See application file for complete search history.

(56) References Cited

U.S. PATENT DOCUMENTS

| 4,261,645 A | 4/1981 | Sawamura et al. |
| 5,482,830 A | 1/1996 | Bogart et al. |
| 5,541,057 A | 7/1996 | Bogart |

(Continued)

FOREIGN PATENT DOCUMENTS

| CN | 102460254 A | 5/2012 |
| CN | 102470167 A | 5/2012 |

(Continued)

OTHER PUBLICATIONS

Avci, O. et al., Interferometric Reflectance Imaging Sensor (IRIS)—A Platform Technology for Multiplexed Diagnostics and Digital Detection, Sensors 15(7):17649-17665 (2015).

(Continued)

*Primary Examiner* — Rebecca M Giere
(74) *Attorney, Agent, or Firm* — COOLEY LLP

(57) ABSTRACT

A spectral reflectance imaging device for detecting nanoparticle exosome biomarker targets includes an illumination source that illuminates a substrate with a plurality of separate wavelengths of incoherent light. The substrate includes an oxide layer and a binding agent to selectively bind nanoparticle exosome biomarker targets to the substrate. An imaging device bindings the light reflected from or transmitted through the substrate and an image processing system detects the nanoparticle exosome biomarker targets a function of the change in reflective properties of the substrate.

18 Claims, 17 Drawing Sheets

(51) Int. Cl.
*G01N 33/543* (2006.01)
*G01N 33/574* (2006.01)

(56) References Cited

U.S. PATENT DOCUMENTS

| | | |
|---|---|---|
| 5,644,388 A | 7/1997 | Maekawa et al. |
| 6,008,892 A | 12/1999 | Kain et al. |
| 6,346,376 B1 | 2/2002 | Sigrist et al. |
| 6,545,758 B1 | 4/2003 | Sandstrom |
| 6,878,523 B2 | 4/2005 | Nelson et al. |
| 7,110,118 B2 | 9/2006 | Unlu |
| 7,173,256 B2 | 2/2007 | Fox |
| 7,208,322 B2 | 4/2007 | Stolowitz et al. |
| 7,227,633 B2 | 6/2007 | Kraus et al. |
| 7,405,819 B2 | 7/2008 | Kraus et al. |
| 7,532,314 B1 | 5/2009 | Black et al. |
| 7,695,680 B2 | 4/2010 | Unlu |
| 7,718,422 B2 | 5/2010 | Chaton et al. |
| 7,737,392 B2 | 6/2010 | Cunningham et al. |
| 7,742,622 B2 | 6/2010 | Lee |
| 7,742,662 B2 | 6/2010 | Cunningham |
| 7,835,013 B2 | 11/2010 | Jones et al. |
| 7,951,583 B2 | 5/2011 | Duer |
| 7,968,836 B2 | 6/2011 | Cunningham et al. |
| 7,988,918 B2 | 8/2011 | Fernandez |
| 8,068,995 B2 | 11/2011 | Chau et al. |
| 8,257,936 B2 | 9/2012 | Laing et al. |
| 8,426,028 B2 | 4/2013 | Cai et al. |
| 8,488,120 B2 | 7/2013 | Hall et al. |
| 8,685,755 B2 | 4/2014 | Ferrari et al. |
| 8,830,481 B2 | 9/2014 | Hall et al. |
| 8,841,137 B2 | 9/2014 | DeLouise et al. |
| 8,846,129 B2 | 9/2014 | Lin et al. |
| 8,852,876 B2 | 10/2014 | Fang et al. |
| 8,969,509 B2 | 3/2015 | Liu et al. |
| 9,410,949 B2 | 8/2016 | Singamaneni et al. |
| 9,599,611 B2 | 3/2017 | Unlu et al. |
| 9,638,632 B2 | 5/2017 | Bornhop |
| 9,803,236 B2 | 10/2017 | Zhang et al. |
| 9,862,987 B2 | 1/2018 | Lo et al. |
| 10,115,013 B2 | 10/2018 | Sibarita |
| 10,151,680 B2 | 12/2018 | Unlu et al. |
| 10,564,107 B2 | 2/2020 | Unlu et al. |
| 10,585,042 B2 | 3/2020 | Unlu et al. |
| 10,928,315 B1 | 2/2021 | Unlu et al. |
| 11,262,359 B2 | 3/2022 | Daaboul et al. |
| 11,275,030 B2 | 3/2022 | Unlu et al. |
| 2003/0010097 A1 | 1/2003 | Porter et al. |
| 2003/0112446 A1 | 6/2003 | Miller et al. |
| 2004/0070764 A1 | 4/2004 | Fujimura et al. |
| 2004/0092028 A1 | 5/2004 | Chaton et al. |
| 2004/0241176 A1 | 12/2004 | Lamparski et al. |
| 2004/0247485 A1 | 12/2004 | Kraus et al. |
| 2004/0252301 A1 | 12/2004 | Kawano et al. |
| 2005/0130174 A1 | 6/2005 | Bao et al. |
| 2005/0266449 A1 | 12/2005 | Kugler et al. |
| 2006/0014232 A1 | 1/2006 | Inagawa et al. |
| 2006/0063188 A1 | 3/2006 | Zanni et al. |
| 2007/0111224 A1 | 5/2007 | Jung et al. |
| 2007/0211985 A1 | 9/2007 | Duer |
| 2007/0278422 A1 | 12/2007 | Einhorn et al. |
| 2009/0226031 A1 | 9/2009 | Izuka |
| 2010/0021954 A1 | 1/2010 | Deshayes et al. |
| 2010/0145627 A1 | 6/2010 | Wang et al. |
| 2010/0184046 A1 | 7/2010 | Klass et al. |
| 2010/0302544 A1 | 12/2010 | Duer |
| 2011/0091377 A1 | 4/2011 | Alani et al. |
| 2011/0091384 A1 | 4/2011 | Alani et al. |
| 2012/0036702 A1 | 2/2012 | Einhorn et al. |
| 2012/0157350 A1 | 6/2012 | True et al. |
| 2012/0164628 A1 | 6/2012 | Duffin et al. |
| 2012/0200694 A1 | 8/2012 | Garsha et al. |
| 2012/0208174 A1 | 8/2012 | Galush et al. |
| 2013/0155499 A1 | 6/2013 | Dixon |
| 2013/0323756 A1 | 12/2013 | Tullis et al. |
| 2014/0377793 A1 | 12/2014 | Bouamrani et al. |
| 2015/0057949 A1 | 2/2015 | Weinberger et al. |
| 2015/0204841 A1 | 7/2015 | Ataullakhanov et al. |
| 2015/0355133 A1 | 12/2015 | Prasad |
| 2016/0017027 A1 | 1/2016 | Azorsa |
| 2016/0257830 A1 | 9/2016 | Singamaneni et al. |
| 2016/0299069 A1 | 10/2016 | Tao et al. |
| 2016/0334398 A1 | 11/2016 | Weissleder et al. |
| 2016/0375439 A1 | 12/2016 | Li et al. |
| 2017/0016821 A1 | 1/2017 | Unlu et al. |
| 2017/0045451 A1 | 2/2017 | Nolan et al. |
| 2017/0067882 A1 | 3/2017 | Bornhop et al. |
| 2017/0116733 A1 | 4/2017 | Juncker et al. |
| 2017/0131267 A1 | 5/2017 | Lee et al. |
| 2017/0234801 A1 | 8/2017 | Unlu et al. |
| 2017/0270690 A1 | 9/2017 | Chung et al. |
| 2017/0370709 A1 | 12/2017 | Mace et al. |
| 2018/0031483 A1 | 2/2018 | Singamaneni et al. |
| 2018/0052425 A1 | 2/2018 | Ozcan et al. |
| 2018/0106759 A1 | 4/2018 | de Oliveira Botelho et al. |
| 2018/0120302 A1 | 5/2018 | Bornhop |
| 2018/0148714 A1 | 5/2018 | Hadrup et al. |
| 2018/0275097 A1 | 9/2018 | Sandoghdar et al. |
| 2018/0321231 A1 | 11/2018 | Singamaneni et al. |
| 2018/0364270 A1 | 12/2018 | Chiu et al. |
| 2018/0372678 A1 | 12/2018 | Patolsky et al. |
| 2019/0049440 A1 | 2/2019 | Singamaneni et al. |
| 2020/0200740 A1 | 6/2020 | Zafiu et al. |

FOREIGN PATENT DOCUMENTS

| | | |
|---|---|---|
| CN | 102753974 A | 10/2012 |
| EP | 2215470 A1 | 8/2010 |
| JP | 2007-101412 A | 4/2007 |
| WO | WO-02/48691 A1 | 6/2002 |
| WO | WO-2004/083820 A2 | 9/2004 |
| WO | WO-2009/048494 A1 | 4/2009 |
| WO | WO-2009/055940 A1 | 5/2009 |
| WO | WO-2010/127001 A1 | 11/2010 |
| WO | WO-2011/000551 A1 | 1/2011 |
| WO | WO-2011/014282 A2 | 3/2011 |
| WO | WO-2011/098509 A1 | 8/2011 |
| WO | WO-2015/031694 A2 | 3/2015 |
| WO | WO-2015/038205 A1 | 3/2015 |
| WO | WO-2015/065995 A1 | 5/2015 |
| WO | WO-2015/085096 A1 | 6/2015 |
| WO | WO-2015/134847 A1 | 9/2015 |
| WO | WO-2016/065487 A1 | 5/2016 |
| WO | WO-2016/164124 A1 | 10/2016 |
| WO | WO-2017/053516 A1 | 3/2017 |
| WO | WO-2017/136676 A1 | 8/2017 |
| WO | WO-2017/196823 A1 | 11/2017 |
| WO | WO-2018/094200 A9 | 8/2018 |
| WO | WO-2018/228625 A1 | 12/2018 |
| WO | WO-2019/144056 A1 | 7/2019 |
| WO | WO-2019/222708 A2 | 11/2019 |
| WO | WO-2019/232321 A1 | 12/2019 |
| WO | WO-2020/160402 A1 | 8/2020 |
| WO | WO-2020/180662 A1 | 9/2020 |

OTHER PUBLICATIONS

Benedikter, B. J. et al., Ultrafiltration combined with size exclusion chromatography efficiently isolates extracellular vesicles from cell culture media for compositional and functional studies, Scientific Reports, 7:1597 (2017).

Carter, E. P. et al., Visualizing Ebolavirus Particles Using Single-Particle Interferometric Reflectance Imaging Snesor (SP-IRIS), Methods in Molecular Biology, 1628:259-270, (2017).

Chan, S. et al., Nanoscale silicon microcavities for biosensing. Materials Science and Engineering C, 15:277-282, (2001).

Cheng, X. R. et al., LED-based interferometric reflectance imaging sensor for the detection of amyloid-13 aggregation, Analyst, 139(1):59-65 (2014).

Collet, J. et al., The elasticity of an individual fibrin fiber in a clot, PNAS, 102(26):9133- 9137, (2005).

(56) References Cited

OTHER PUBLICATIONS

Cretich et al., Silicon biochips for dual label-free and fluorescence detection: Application to protein microarray development, Biosensors and Bioelectronics, 26(9):3938-3943, (2011).
Cretich, M. et al., Digital detection of biomarkers assisted by nanoparticles: application to diagnostics, Trends in Biotechnology, 33(6):343-351 (2016).
Cretich, M. et al., Interferometric silicon biochips for label and label-free DNA and protein microarrays, Proteomics, 12:2963-2977, (2012).
Daaboul, G. et al., Digital detection of exosomes by interferometric imaging, Nature Sci. Rep., 6:37246, (2016). PMID: 27853258. (PMCID in process).
Daaboul, G. G. et al., Digital Sensing and Sizing of Vesicular Stomatitis Virus Pseudotypes in Complex Media; A model for Ebola and Marburg Detection, ACS Nano, 8(6):6047-6055, (2014).
Daaboul, G. G. et al., Enhanced light microscopy visualization of virus particles from Zika virus to filamentous ebolaviruses, PLoS One, 12(6):e0179728:1-15, (2017).
Daaboul, G. G. et al., High-Throughput Detection and Sizing of Individual Low-Index Nanoparticles and Viruses for Pathogen Identification, Nano Letters, 10:4727-4731, (2010).
Daaboul, G. G. et al., LED-Based Interferometric Reflectance Imaging Sensor for quantitative dynamic monitoring of biomolecular interactions, Biosensors and Bioelectronics, 26(5):2221-2227, (2011).
Diaz, G. et al., Protein Digestion, Ultrafiltration, and Size Exclusion Chromatography to Optimize the Isolation of Exosomes from Human Blood Plasma and Serum, Journal of Visualized Experiments, 134(e57467):1-6 (2018).
Emsley, M. K. et al., Silicon Substrates With Buried Distributed Bragg Reflectors for Resonant Cavity-Enhanced Optoelectronics, IEEE Journal of Selected Topics in Quantum Electronics, 8(4):948-955, (2002).
European Search Report, Application No. 17709500.7 (Detection of Exosomes Having Surface Markers, filed Feb. 3, 2017), issued by European Patent Office, 2 pages, Sep. 13, 2019.
Gagni et al., Combined mass quantitation and phenotyping of intact extracellular vesicles by a microarray platform, Analytica Chimica Acta, 02:160-167, (2015).
Gannavarpu, R. et al., Spatiotemporal Characterization of a Fibrin Clot Using Quantitative Phase Imaging, PLOS ONE, 9(11):e111381:1-7, (2014).
Gong et al., Microparticles in cancer: A review of recent developments and the potential for clinical application, Seminars in Cell & Developmental Biology, 40:35-40, (2014).
Hetagan, A. et al., Visualization of the dynamics of fibrin clot growth 1 molecule at a time by total internal reflection fluorescence microscopy, Blood, 121(8):1455-1458, (2013).
International Search Report for PCT/2016/053015, 2 pages (mailed Dec. 9, 2016).
International Search Report, PCT/US2017/016434 (Detection of Exosomes Having Surface Markers, filed Feb. 3, 2017), 7 pages, Jul. 13, 2017.
Jamur, MC and Oliver C., Premeabilization of cell membranes, Methods in Molecular Biology, 588:63-66, (2010).
Jenison, R. et al., Interference-based detection of nucleic acid targets on optically coated silicon, Nature Biotechnology, 19:62-65, (2001).
Jorgensen, A. P. et al., Extracellular Vesicle (EV) Array: microarray capturing of exosomes and other extracellular vesicles for multiplexed phenotyping, Journal of Extracellular Vesicles, 2(1):1-9, (2013).
Kedersha, N., Immunofluorescence: Tips for immunostaining cultured cells, Proteintech Group, [retrieved on Feb. 6, 2020 <https://www.ptglab.com/news/blog/immunofluorescence-tips-for-immunostaining-cultured-cells/>], 7 pages, (2015).
Lancé, Marcus D., A general review of major global coagulation assays: thrombelastography, thrombin generation test and clot waveform analyasis, Thrombosis Journal, 13:1-6, (2015).
Lu, J. et al., Reflective Interferometric Detection of Label-Free Oligonucleotides, Analytical Chemistry, 76:4416-4420, (2004).
Matsuura, M. and Kishi, N., Frequency Control Characteristics of a Single-Frequency Fiber Laser with an External Light Injection, IEEE Journal of Selected Topics in Quantum Electronics, 7(1):55-58. (2001).
Melo, S.A. et al., Glypican-1 identifies cancer exosomes and detect early pancreatic cancer, Nature, 523(7559):177-182 (2015).
Moiseev, L. et al., DNA conformation on surfaces measured by fluorescence self-interference, Proceedings of the National Academy of Sciences, 103(8):2623-2628, (2006).
Monroe, M. R. et al., Single Nanoparticle Detection for Multiplexed Protein Diagnostics with Attomolar Sensitivity in Serum and Unprocessed Whole Blood, Anal. Chem. 85(7):3698-3706, (2013).
Nikitin, P. I. et al., New direct optical biosensors for multi-analyte detection, Sensors and Actuators B, 90:46-51, (2003).
Ozkumur, E. et al., Label-free microarray imaging for direct detection of DNA hybridization and single-nucleotide mismatches, Biosens. Bioelectron., 25(7):1789-1795, (2010). PMCID: PMC2824047.
Partial Search Report with Provisional Opinion, PCT/US2017/016434 (Detection of Exosomes Having Surface Markers, filed Feb. 3, 2017), 16 pages, May 18, 2017.
Piehler, J. et al., Affinity Detection of Low Molecular Weight Analyties, Anal. Chem., 68:139-143, (1996).
Prestrelski, S.J. et al., Dehydration-induced Conformational Transitions in Proteins and their Inhibitions by Stabilizers, Biophysical Journal, 65:661-671, (1993).
Properzi et al., Exosomes: the future of biomarkers in medicine, Biomarkers in Medicine, 84(3):177-189, (2008).
Rambaran, Roma N. and Serpell, Louise C., Amyloid fibrils, Abnormal protein assembly, PRION, 2(3):112-117, (2008).
Rao, et al., Biophysical Properties of Nucleic Acids at Surfaces Relevant to Microarray Performance, Biomater Sci, 2(4):436-471 (2014).
Reddington, A. P. et al., An Interferometric Reflectance Imaging Sensor for Point of Care Viral Diagnostics, IEEE Transactions on Biomedical Engineering, 60(12):3276-3282 (2013).
Sandstrom, T. et al., Visual detection of organic monomolecular films by interference colors, Applied Optics, 24:472-479, (1985).
Scherr, S. M. et al., Real-Time Capture and Visualization of Individual Viruses in Complex Media, ACS Nano, 10(2):2827-2833, (2016).
Shao et al., Protein typing of circulating microvesicles allows real-time monitoring of glioblastoma therapy, Nature Medicine, 18(12):1835-1841, (2012).
Su, J. et al., Label-free detection of single nanoparticles and biological molecules using microtoroid optical resonators, Light: Science & Application, 5(1):e16001 (2016).
Thermofisher Scientific, Invitrogen, Alix Plycolonal Anitbiody, retrieved Feb. 25, 2019 [<https://www.thermofisher.com/antibody/product/Alix-Antibody-Polyclonal/PA5-52873>], 4 pages.
Thermofisher Scientific, Invitrogen, Syndecan 4 Polyclonal Antibody, retrieved Feb. 25, 2019 [<https://www.thermofisher.com/antibody/product/Syndecan-4-Antibody-Polyclonal/36-3100>], 5 pages, (2014).
Trune, D. R. et al., Simultaneous measurement of multiple ear proteins with multiplex elisa assays, Hear Res. 275:1-7, (2011).
Van Der Pol, E. et al., Optical and non-optical methods for detection and characterization of microparticles and exosomes, Journal of Thrombosis and Haemostatsis, 8(12):2596-2607 (2010).
Visser, D. et al., Optical properties and fabrication of dielectric metasurfaces based on amorphous silicon nanodisk arrays, Optics Express, 27(4):5353-5367 (2019).
Vlassov et al., Exosomes: current knowledge of their composition, biological functions, and diagnostic and therapeutic potentials, Biochimica et Biophysica Acta (BBA)-General Subjects, 1820(7):940-948, (2012).
Wang et al., Local and Global Anatomy of Antibody-Protein Antigen Recognition, J Mol Recognit. 31(5):e2693, doi:10.1002/jmr.2693, (2018).
Wikipedia, Green fluorescent protein, retrieve Feb. 25, 2019, [<https://en.wikipedia.org/wiki/Green_fluorescent_protein>], 19 pages.

(56) References Cited

OTHER PUBLICATIONS

Wikipedia, Oligonucleotide, retrieved Feb. 25, 2019, [<https://en.wikipedia.org/wiki/Oligonucleotide>], 4 pages.
Wikipedia, Syntenin-1, 8 pages, retrieved Feb. 25, 2019 [<https://en.wikipedia.org/wiki/Syntenin-1>].
Wikipedia, TSG101, retrieved Feb. 25, 2019, [<https://en.wikipedia.org/wiki/TSG101>], 12 pages.
Written Opinion for PCT/2016/053015, 4 pages (mailed Dec. 9, 2016).
Written Opinion, PCT/US2017/016434 (Detection of Exosomes Having Surface Markers, filed Feb. 3, 2017), 14 pages, Jul. 13, 2017.
Yeromonahos, C. et al., Nanostructure of the Fibrin Clot, Biophysical Journal, 99:2018-2027, (2010).
Yurt et al., Single nanoparticle detectors for biological applications, Nanoscale 4(3):715-726, (2012).
Zarovni N., et al., Integrated isolation and quantitative analysis of exosome shuttled proteins and nucleic acids using immunocapture approaches, Methods, 87:46-58 (2015).
Zhu, L. et al., Label-Free Quantitative Detection of Tumor-Derived Exosomes through Surface Plasmon Resonance Imaging, Analytical Chemistry, 86(17):8857-8864 (2014).

SPECTRAL REFLECTANCE CHIP READER

SPECTRAL REFLECTANCE CHIP

SPECTRAL REFLECTANCE CASSETTE

AN ARRAY OF BINDING PROBES SPATIALLY SEPARATED

DETECTION OF EXOSOMES HAVING SURFACE MARKERS

CROSS-REFERENCE TO RELATED APPLICATIONS

This application is a divisional of U.S. patent application Ser. No. 16/074,259, filed Jul. 31, 2018, which is a U.S. National Phase Entry of PCT Application No. PCT/US2017/016434, filed Feb. 3, 2017, which claims the benefit of U.S. Application Ser. No. 62/291,848 filed on Feb. 5, 2016, the disclosures of each of which are hereby incorporated by reference in their entirety

FIELD OF THE INVENTION

The present invention relates generally to the detection of particles (e.g., nanoparticles, e.g., exosomes, e.g., extracellular vesicles) comprising biomolecules, e.g., biomolecules associated with cancer, e.g., pancreatic cancer.

BACKGROUND OF THE INVENTION

The ability to detect biological target molecules as well as nanomolecular particles is fundamental to our understanding of both cell physiology and disease progression, as well as for use in various applications such as early and rapid evaluation, e.g., diagnosis of, disease. There is a need for systems and methods for detecting nanomolecular particles with high sensitivity and specificity for the diagnosis, staging, or determination of risk of disease in a subject.

SUMMARY OF THE INVENTION

Exosomes are small lipid-bilayer enclosed extracellular vesicles ranging from approximately 30-200 nm in size that circulate in the blood. Exosomes are secreted by numerous cell types, including cancer cells. Exosomes derived from cancer cells are specifically enriched for the cell surface proteoglycan, glypican-1 (GPC1), among other proteins from the glypican family. Described herein are methods of using glypican-positive (e.g., GPC1-positive) enriched exosomes as a non-invasive evaluation, diagnostic, and screening tool, and devices to perform such methods. For example, methods and devices described herein include methods of evaluating a sample, evaluating a subject, or diagnosing a subject, comprising: contacting a sample from the subject with a binding agent, e.g., a binding agent specific for glypican-1, disposed on a substrate, e.g., a substrate comprising an essentially planar surface, under conditions suitable for binding of a circulating extracellular vesicle, e.g., an exosome, in the sample to a binding agent; determining if a circulating extracellular vesicle, e.g., an exosome, e.g., an exosome comprising glypican-1, is bound to the binding agent, thereby evaluating the sample, evaluating a subject, or diagnosing a subject.

In certain embodiments, a method or device described herein can operate under interferometric principles of detection, using non-laser light sources, such as LEDs, as the illumination source. LEDs are very low-cost, compact, and robust and are ideal for large scale use and distribution for diagnostic and research applications. Certain embodiments described herein incorporate quantitative molecular binding measurements obtained through a substrate microarray imaging system, with the capability to use low-cost incoherent illumination sources that enable, high magnification for detection of single biomolecular targets found in a sample.

Substrate enhanced microarray imaging has the capability to detect the binding of biomolecules to a surface at tens of thousands of spots simultaneously in a label-free fashion. In certain embodiments, the device described herein includes an incoherent light source, such as a light-emitting diode (LED), which can be utilized as the illumination source for interferometric principles of detection and measurement. LEDs are very low-cost, compact, and robust, and are thus ideal for large-scale use and distribution for diagnostic and research applications. These devices and associated methods provide a low-cost incoherent illumination source that enables a high magnification embodiment for detection and imaging of nanoparticles, e.g., extracellular vesicles, e.g., exosomes comprising biomarkers, in a sample.

In certain embodiments, the devices described herein facilitate a method of using LED illumination for substrate enhanced detection of nanoparticle extracellular vesicles such as exosome biomarkers bound to a surface. Described herein, in one aspect, is a high-throughput spectroscopy device that facilitates a method for simultaneously recording a response of an entire substrate surface, comprising using at least one incoherent illumination light source and imaging the reflected or transmitted light by an imaging device. In certain embodiments, at least one incoherent illumination light source is centered around 420 nm, as provided herein. In certain embodiments, the substrate comprises a transparent layer than is 60 nm thick, as provided herein.

In one aspect, the invention is directed to a method of isolating cancer-derived circulating extracellular vesicles (e.g., exosomes) comprising: contacting a sample obtained from a subject with a surface of a substrate, wherein the surface of the substrate optionally comprises one or more binding agents specific for one or more glypicans expressed on a surface of the circulating extracellular vesicles, to bind (e.g., via adsorption, e.g., via the one or more binding agents) (e.g., non-covalently, e.g., covalently) circulating extracellular vesicles present in the sample to the surface of the substrate, thereby isolating the extracellular vesicles; and detecting the extracellular vesicles bound to the surface of the substrate.

In another aspect, the invention is directed to a method of isolating circulating extracellular vesicles (e.g., cancer-derived circulating extracellular vesicles) (e.g., exosomes) comprising: contacting a sample obtained from a subject with a surface of a substrate, wherein the surface of the substrate optionally comprises a first set of one or more binding agents specific for one or more glypicans expressed on a surface of the circulating extracellular vesicles, to bind (e.g., via adsorption, e.g., via the one or more binding agents) (e.g., non-covalently, e.g., covalently) circulating extracellular vesicles present in the sample to the surface of the substrate, thereby isolating the extracellular vesicles; contacting the sample with a second set of one or more binding agents (e.g., prior to binding of any circulating extracellular vesicles present in the sample to the surface of the substrate) (e.g., post binding of any circulating extracellular vesicles present in the sample to the surface of the substrate); detecting the extracellular vesicles bound to the surface of the substrate.

In certain embodiments, the one or more glypicans comprise a member selected from the group consisting of glypican-1, glypican-2, glypican-3, glypican-4 glypican-5, and glypican-6).

In certain embodiments, the one or more glypican comprises or is glypican-1. In certain embodiments, one or more glypican comprises or is glypican-3.

In certain embodiments, the cancer comprises adenocarcinoma. In certain embodiments, the cancer comprises lung cancer. In certain embodiments, the lung cancer comprises a non-small cell lung cancer or a small cell lung cancer. In certain embodiments, the cancer comprises a member selected from the group consisting of esophageal, ovarian, colon, pancreatic, lung, breast, tracheal, brain, liver, bladder, stomach, uterine, cervical, testicular, rectal, skin, and prostate cancer.

In certain embodiments, the method comprises evaluating the level (e.g., quantity, e.g., number, e.g., concentration) of circulating extracellular vesicles in the sample. In certain embodiments, the method comprises evaluating a number of circulating extracellular vesicles bound to the substrate or a predetermined portion or area of the substrate, present in the sample, or present in the subject from which the sample is obtained.

In certain embodiments, the method comprises providing a value for a parameter (e.g., an abundance-parameter) related to the number of circulating extracellular vesicles bound to the substrate or a predetermined portion or area of the substrate, present in the sample, or present in the subject from which the sample is obtained.

In certain embodiments, the method comprises determining size of the circulating extracellular vesicles bound to the substrate (e.g., diameter, e.g., volume) or a predetermined portion or area of the substrate, present in the sample, or present in the subject from which the sample is obtained (e.g., wherein the diameter is from about 10 nm to about 3100 nm, e.g., from about 50 nm to about 2000 nm, e.g., from about 50 nm to about 1000 nm, e.g., from about 20 nm to about 300 nm, e.g., from about 30 nm to about 100 nm, e.g., from about 50 nm to about 200 nm, e.g., from about 200 nm to about 3000 nm).

In certain embodiments, the size is the average size of the extracellular vesicles bound to the substrate or a predetermined portion or area of the substrate.

In certain embodiments, the method comprises providing a value for a parameter (a size parameter) related to the diameter of an extracellular vesicle bound to the substrate or a predetermined portion or area of the substrate, present in the sample, or present in the subject from which the sample is obtained.

In certain embodiments, the method comprises comparing a value for an abundance parameter, a size parameter (e.g., a diameter parameter, e.g., a volume parameter), or a parameter related to both size and abundance, with a reference value (e.g., thereby evaluating the sample, e.g., thereby characterizing the sample, e.g., thereby diagnosing the subject).

In certain embodiments, if a value for one or more of an abundance parameter, a size parameter, or a parameter related to both size and abundance, meets a predetermined relationship with a reference value, classifying the sample or subject. In certain embodiments, if a value for a one or more of an abundance parameter, a size parameter, or a parameter related to both size and abundance, is greater than a reference value, classifying the sample or subject, e.g., classifying the subject as at risk for or having cancer.

In certain embodiments, the reference value is a value determined for a subject not having a preselected disorder, e.g., a cancer. In certain embodiments, the reference value is a function of one or more of an abundance parameter, a diameter parameter, or a parameter related to both diameter and abundance, from a subject not having a preselected disorder, e.g., a cancer.

In certain embodiments, the value for one or more of an abundance parameter, a diameter parameter, or a parameter related to both diameter and abundance, is greater than a reference value, and the subject is classified as being at risk for or having pancreatic cancer, e.g., pancreatic adenocarcinoma. In certain embodiments, if a value for a one or more of an abundance parameter, a diameter parameter, or a parameter related to both diameter and abundance, is greater than a reference value, classifying the sample or subject, e.g., classifying the subject as at risk for or having cancer.

In certain embodiments, the sample is classified as being indicative of any one of or combination of the following: a) the absence of a preselected cancer (e.g., pancreatic cancer, e.g., pancreatic adenocarcinoma, e.g., breast cancer, e.g., lung cancer, e.g., colon cancer, e.g., glioblastoma, e.g., ovarian cancer); b) the presence of the preselected cancer; c) the presences of a non-cancerous disorder of a preselected tissue (e.g., the pancreas, e.g., lung, e.g., colon, e.g., breast, e.g., brain, e.g., ovary); or d) the presence of a preselected pre-cancerous lesion of the preselected tissue.

In certain embodiments, the subject is classified as being at an elevated chance of any one of or the combination of the following: a) not having the preselected cancer; b) having the preselected cancer; c) having the non-cancerous disorder of the preselected tissue; or d) having the preselected pre-cancerous lesion of the preselected tissue.

In certain embodiments, the method comprises monitoring or evaluating the progress or state of the preselected cancer.

In certain embodiments, the value for one or more of an abundance parameter, a size parameter, or a parameter related to both size and abundance, is correlated with the progress or state of the preselected cancer.

In certain embodiments, the method comprises, responsive to the evaluation, classification, or diagnosing, selecting a treatment option for the subject.

In certain embodiments, the method comprises treating the subject, e.g., for cancer (e.g., wherein the cancer comprises a member selected from the group consisting of esophageal, ovarian, colon, pancreatic, lung, breast, tracheal, brain, liver, bladder, stomach, uterine, cervical, testicular, rectal, skin, and prostate cancer).

In certain embodiments, the one or more binding agents comprise a member selected from the group consisting of an antibody molecule, a nucleic acid, a polypeptide, and an aptamer.

In certain embodiments, the antibody molecule comprises a member selected from the group consisting of a monoclonal antibody, a polyclonal antibody, and antigen binding fragment thereof (e.g., wherein the one or more binding agents comprise a rodent, rabbit, mouse, or rat, anti-human antibody or binding fragment thereof).

In certain embodiments, the antibody molecule specifically binds an antigen found on the surface of a cancer cell (e.g., a glypican (e.g., wherein the glypican comprises a member selected from the group consisting of glypican-1, glypican-2, glypican-3, glypican-4, glypican-5, and glypican-6) (e.g., wherein the antibody molecule specifically binds an extracellular portion of the glypican)).

In certain embodiments, a first binding agent that is bound to the surface of the substrate (e.g., a first binding agent that binds an extracellular portion of glypican-1, e.g., a binding agent that binds an extracellular portion of glypican-3 to the surface of the substrate) is different from a second binding agent that to a protein on a surface of the circulating extracellular vesicles (e.g., that binds an extracellular portion of glypican-3, e.g., that binds an extracellular portion of glypican-1) (e.g., wherein the protein comprises a member selected from the group consisting of CD63, CD81, CD9, Flotillin-1, Mannose binding lectins, and lectins) (e.g., wherein the second binding agent is cancer or disease specific) (e.g., wherein the second binding agent binds the circulating extracellular vesicle prior to binding to the surface of the substrate) (e.g., wherein the second binding agent is attached to a label (e.g., a nanoparticle, e.g., a fluorophore).

In certain embodiments, the circulating extracellular vesicle is from a pancreatic cancer cell. In certain embodiments, the circulating extracellular vesicle is from a breast cancer cell.

In certain embodiments, the body fluid comprises plasma, serum, whole blood, saliva, cerebrospinal fluid (CSF), or urine.

In certain embodiments, the sample is evaluated with reflectance imaging system, e.g., an imaging system described herein.

In certain embodiments, the spectral reflectance imaging system comprises: a substrate having a first reflective surface and a partially transparent layer providing a second reflective surface; a biolayer bound comprising the first set of the one or more binding agents to the second reflective surface; an illumination source, e.g., an illuminating source comprising at least one light source that provides light in a narrow frequency band and directing the frequency band of light at the substrate (e.g., wherein one of the narrow frequency band comprises a range of wavelengths from about 300 nm to about 800 nm, e.g., from about 400 nm to about 600 nm, e.g., from about 405 nm to about 455 nm, e.g., about 420 nm); and an imaging device directed at the second reflective surface of the substrate and adapted to produce imaging signals representative of light from the illumination source being reflected by the first reflective surface; the second reflective surface; and scattered light by particle(s) on the second surface.

In certain embodiments, the first reflective surface is a silicon substrate and the transparent layer is silicon oxide ($SiO_2$).

In certain embodiments, the spectral reflectance imaging system further comprising an image acquisition and processing system, coupled to the imaging device and adapted to receive the imaging signals and under program control, produce an image of the biolayer/and or particle(s) on the second reflective surface.

In certain embodiments, the transparent layer is from about 10 nm thick to about 100 nm thick, e.g., from about 40 nm thick to about 70 nm thick, e.g., about 60 nanometers thick).

In certain embodiments, the method comprises providing a first specular reflecting interface of the substrate with a binding agent for binding a circulating extracellular vesicle (e.g., an exosome comprising a glypican), to the first specular reflecting interface of the substrate; providing a second specular reflecting interface that is substantially parallel to and underlies the first specular reflecting interface; illuminating the surface with light substantially centered around one or more wavelengths of light; imaging light reflected or transmitted from the substrate using an imaging device; producing a spectral reflectance image of the surface of the substrate; and correlating the features (e.g., diameter of the circulating extracellular vesicles) on the image to discrete circulating extracellular vesicles on the surface (e.g., thereby evaluating the size of each of the discrete circulating extracellular vesicles).

In certain embodiments, the transparent layer is about 60 nm thick, wherein one of the narrow frequency band is 420 nm (e.g., wherein the imaging occurs while the substrate is immersed in aqueous solution, e.g., wherein the imaging occurs after drying the substrate).

In certain embodiments, the imaging device comprises a camera having a high magnification objective lens with a high numerical aperture.

In certain embodiments, each wavelength of light is produced by a separate, narrow band light source.

In certain embodiments, the imaging device is a monochromatic CCD or CMOS camera.

In certain embodiments, the surface is illuminated by a light source from a standard bright-field microscope optical setup, and wherein the reflected light is transmitted to an eyepiece.

In certain embodiments, each wavelength of light is produced by a separate light emitting diode (LED), each having a different emission peak wavelengths, and wherein the imaging device is a monochromatic camera.

In certain embodiments, the imaging device is a monochromatic CCD or CMOS camera.

In certain embodiments, the layered substrate comprises anywhere from about 30-100 nm (e.g., about 60 nm) of $SiO_2$ layered on a Si wafer. In certain embodiments, the surface is illuminated with white light and the imaging device includes a color camera. In certain embodiments, the surface is illuminated by an RGB (red green blue) LED and the imaging device includes a color camera. In certain embodiments, the surface is illuminated by a broadband light source.

In certain embodiments, the camera further comprises a spatial filter on the camera's optical axis.

In certain embodiments, the light is incoherent.

In certain embodiments, each wavelength of light is produced by a separate, narrow band light source or by a broadband light source.

In certain embodiments, each wavelength of light is produced by a separate light emitting diode (LED), each having a different emission peak wavelength.

In certain embodiments, the imaging device comprises a member selected from the group consisting of a monochromatic CCD camera, a CMOS sensor, and a color camera. In certain embodiments, the camera further comprises a spatial filter on the camera's optical axis.

In certain embodiments, detecting the particle comprises detecting the binding of the particle on the surface of the layered substrate.

In certain embodiments, the surface of the layered surfaces comprises a binding agent for binding a predefined particle and the solution comprises at least one predefined particle.

In another aspect, the invention is directed to a substrate, e.g., a substrate described herein, having disposed thereon a binding agent described herein, e.g., a binding agent, e.g., an antibody molecule, specific for glypican (e.g., glypican-1, e.g., glyican-2, e.g., glypican-3, e.g., glypican-4, e.g., glypican-5, e.g., glypican-6). In certain embodiments, the substrate comprises an circulating extracellular vesicle (e.g., an exosome) bound to the binding agent.

In another aspect, the invention is directed to a spectral reflectance imaging system comprising: a substrate having a first reflective surface and a thin semi-transparent layer providing a second reflective surface; a biolayer bound to the second reflective surface comprising one or more binding agents specific for glypican (e.g., glypican-1, e.g., glypican-2, e.g., glypican-3, e.g., glypican-4, e.g., glypican-5, e.g., glypican-6); an illumination source comprising at least one light source providing light in one narrow frequency band and directing the frequency band of light at the substrate; and an imaging device directed at the second reflective surface of the substrate and adapted to produce imaging signals representative of light from the illumination source being reflected by the first reflective surface and the second reflective surface.

In certain embodiments, the first reflective surface is a silicon substrate and the semi-transparent layer is silicon oxide ($SiO_2$).

In certain embodiments, the system comprises an image acquisition and processing system, coupled to the imaging device and adapted to receive the imaging signals and under program control, produce an image of the biolayer on the second reflective surface.

In certain embodiments, the illumination source produces white light and the system further includes a color wheel having at least one filter, each producing a beam of light in one of at least three narrow frequency bands that is directed at the substrate.

In another aspect, the invention is directed to a cassette for analysis via the spectral reflectance imaging system the cassette comprising a substrate (e.g., a substrate described herein) having disposed thereon a binding agent (e.g., an antibody molecule) specific for an antigen found on the surface of a cancer cell (e.g., glypican (e.g., glypican-1, e.g., glypican-2, e.g., glypican-3, e.g., glypican-4, e.g., glypican-5, e.g., glypican-6)).

In another aspect, the invention is directed to a method for detecting the binding of a circulating extracellular vesicle (e.g., exosomes) to a surface of a substrate, the method comprising: providing a first specular reflecting interface of the substrate with one or more binding agents (e.g., a binding agent specific for glypican (e.g., glypican-1, e.g., glypican-2, e.g., glypican-3, e.g., glypican-4, e.g., glypican-5, e.g., glypican-6)) to the first specular reflecting interface of the substrate; providing a second specular reflecting interface that is substantially parallel to and underlies the first specular reflecting interface; illuminating the surface with light substantially centered around one or more wavelengths; imaging light reflected or transmitted from the substrate using an imaging device; producing an image of the surface of the substrate; and correlating the features on the image to discrete circulating extracellular vesicle biomarkers (glypican (e.g., glypican-1, e.g., glypican-2, e.g., glypican-3, e.g., glypican-4, e.g., glypican-5, e.g., glypican-6)) on the surface.

In certain embodiments, the imaging device comprises a camera having a high magnification objective lens with a high numerical aperture.

In certain embodiments, each wavelength of light is produced by a separate, narrow band light source.

In certain embodiments, the imaging device is a monochromatic CCD or CMOS camera.

In certain embodiments, the surface is illuminated by a light source from a standard bright-field microscope optical setup, and wherein the reflected light is transmitted to an eyepiece.

In certain embodiments, each wavelength of light is produced by a separate light emitting diode (LED), each having a different emission peak wavelengths, and wherein the imaging device is a monochromatic camera.

In certain embodiments, the imaging device is a monochromatic CCD or CMOS camera.

In certain embodiments, the layered substrate comprises anywhere in a range of 30-100 nm of $SiO_2$ layered on a Si wafer (e.g., 60 nm).

In certain embodiments, the surface is illuminated with white light and the imaging device includes a color camera.

In certain embodiments, the surface is illuminated by an RGB (red green blue) LED and the imaging device includes a color camera.

In certain embodiments, the surface is illuminated by a broadband light source.

In certain embodiments, the camera further comprises a spatial filter on the camera's optical axis.

In another aspect, the invention is directed to a method for detecting a particle on a surface of a layered substrate comprising: providing the surface of the layered substrate with a binding agent, e.g., a binding agent specific for glypican (e.g., glypican-1, e.g., glypican-2, e.g., glypican-3, e.g., glypican-4, e.g., glypican-5, e.g., glypican-6); contacting a solution having at least one circulating extracellular vesicle comprising an exosome biomarker (glypican (e.g., glypican-1, e.g., glypican-2, e.g., glypican-3, e.g., glypican-4, e.g., glypican-5, e.g., glypican-6)), with the surface of the substrate; illuminating the surface with at least one wavelength of light; imaging the light reflected or transmitted from the substrate using an imaging device; and producing an image of the surface of the substrate to detect the extracellular circulating vesicle (e.g., exosome) on the surface of the layered substrate.

In certain embodiments, the layered substrate comprises $SiO_2$ layered on a Si substrate.

In certain embodiments, the light is incoherent.

In certain embodiments, each wavelength of light is produced by a separate, narrow band light source.

In certain embodiments, each wavelength of light is produced by a separate light emitting diode (LED), each having a different emission peak wavelength. In certain embodiments, each wavelength of light is produced by a white light source. In certain embodiments, each wavelength of light is produced by a standard bright-field microscope optical setup, and wherein the reflected light is transmitted to an eyepiece.

In certain embodiments, the imaging device is a monochromatic CCD camera or a color camera. In certain embodiments, the color camera is a 3-D CCD camera. In certain embodiments, the imaging device comprises a camera having a high magnification objective lens with a high numerical aperture. In certain embodiments, the camera further comprises a spatial filter on the camera's optical axis. In certain embodiments, detecting the particle comprises detecting the binding of the exosome nanoparticle on the surface of the layered substrate.

In certain embodiments, the method comprises sequentially illuminating the substrate with light at increasing wavelengths for each subsequent illumination (e.g., wherein each subsequent illuminated wavelength of the plurality of wavelengths has a longer wavelength than the previously illuminated wavelength) (e.g., wherein each of the plurality of wavelengths is within a range from about from about 500 nm to about 750 nm, e.g., from about 525 nm to about 700 nm) (e.g., wherein the first wavelength of the plurality of wavelengths is about 420 nm, e.g., wherein the second wavelength of the plurality of wavelengths is about 535 nm).

Elements of embodiments involving one aspect of the invention (e.g., methods) can be applied in embodiments involving other aspects of the invention, and vice versa.

BRIEF DESCRIPTION OF THE FIGURES

The foregoing and other objects, aspects, features, and advantages of the present disclosure will become more apparent and better understood by referring to the following description taken in conduction with the accompanying drawings, in which:

FIG. 8A shows a schematic of a substrate that is functionalized with a binding agent or a combination of multiple binding agents (e.g., protein markers such as anti-CD63, anti-CD9, anti-CD81, Tim-4 and anti-flotillin-1; e.g., carbohydrate binding lectins such as *Galanthus nivalis* lectin (GNA)), according to an illustrative embodiment on the invention.

FIG. 8B shows a schematic where a combination of markers can be mixed and then immobilized on a substrate, according to an illustrative embodiment of the invention. The substrate is functionalized with two or more binding agents that are mixed together.

FIG. 8C shows a schematic where a sample is contacted with the functionalized substrate to isolate extracellular vesicles and exosomes, according to an illustrative embodiment of the invention. The amount of captured vesicles can be quantified using an interferometric biosensor (e.g., SP-IRIS).

DETAILED DESCRIPTION

Figure 1:
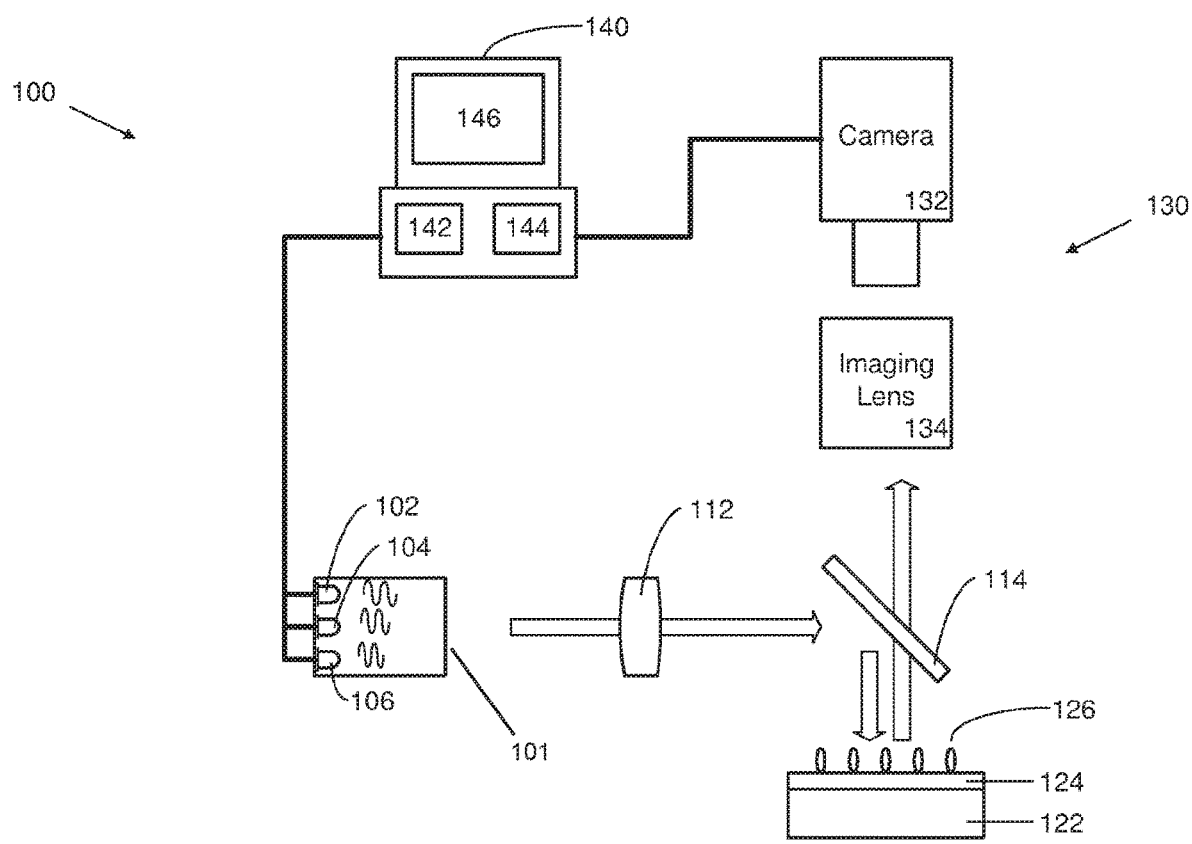
FIG. 1 shows a diagrammatic view of a spectral reflectance imaging system for making interferometric measurements according to an illustrative embodiment of the invention.

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

In one or more embodiments, the invention is directed to an apparatus that can detect binding of nanoparticle extracellular vesicles such as exosomes to binding agents on a surface of a substrate. The binding agents can be immobilized on a layered substrate surface that has a spectral reflectance signature that is altered upon immobilization of said nanoparticles on a binding layer on the substrate surface. In particular, as will be described herein, the image processing system detects the extracellular vesicles a function of the change in reflective properties of the substrate and an image processing system comprises a forward model to provide accurate and quantitative sizing of the extracellular vesicles. In particular, a preferred embodiment of the device uses a single wavelength (band) of light to measure the interference/mixing of reflected light from the binding layer with the scattered light from the particle (scattering of the light). As extracellular vesicles bind to the binding layer, the scattered light from these objects interfere with the reflected light from the substrate surface making the extracellular vesicles observable on an imaging device as discrete objects (dots). The substrate is illuminated with one (or more) wavelengths of light, and if one or more extracellular vesicle objects in the sample binds with the binding layer, the nanoparticle target will appear in the image as single discrete objects, thereby allowing the detection of the individual binding of the nanoparticle targets as well as the quantitative sizing of the extracellular vesicles. The apparatus allows for the simultaneous imaging of the entire field of view of a surface for high-throughput applications. The apparatus and method has several advantages such as low-cost, high-throughput, rapid and portable detection.

Also described herein are methods of use of the device for the detection of a variety of biomolecular targets. In some aspects, the devices and methods described herein provide a high-throughput method for simultaneously recording a response of an entire substrate surface, comprising sampling at least one wavelength using a light source providing incoherent light, and imaging the reflected or transmitted light using an imaging device. The device can include a light-emitting diode (LEDs) as the illumination source for interferometric principles of detection. Interferometric measurements can provide desired sensitivity and resolution using optical path length differences (OPD).

Accordingly, described herein are devices and methods for substrate enhanced detection of binding of molecules or nanoparticles or extracellular vesicles such as exosomes to a surface of a substrate. The device samples the reflectance spectrum by illuminating the substrate with at least one wavelength of light, using, for example, an LEDs and recording the reflectance by an imaging device, such as a 2-D arrayed pixel camera. In this way, the reflectance spectrum for the whole field-of-view is recorded simultaneously. Using this device and method, high-throughput microarray imaging can be accomplished. The invention can also provide high-magnification imaging for detection of biomolecular nanoparticle targets in the 30 nm to a few (2-3) microns in range. Such high-magnification detection can be used, for example, for the detection of a single particle on a capture surface.

The instrument and process provide a high-throughput spectroscopy technique where sampling at least one wavelength is realized by using a narrowband light sources, such as an LED, and the reflected or transmitted light is imaged to an imaging device, such as a monochromatic CCD camera, thus allowing the response of the entire imaged surface to be recorded simultaneously. The microarray can be fabricated on a layered substrate (for example: anywhere from a few nm of $SiO_2$ up to 100 nm of $SiO_2$ layered on a Si wafer). A preferred embodiment includes a green LED light source (535 nm) and 100 nm oxide of $SiO_2$ layered on a Si wafer. A second preferred embodiment includes an ultraviolet LED light source (420 nm) and 60 nm oxide of $SiO_2$ layered on a Si wafer. A third preferred embodiment, for use when imaging in complex media, includes an ultraviolet LED light source (420 nm) and 30-to-60 nm oxide of $SiO_2$ layered on a Si wafer.

FIG. 1 illustrates a diagrammatic view of a spectral reflectance imaging system 100 according to an embodiment of the present invention. The system 100 can include an illumination source 101, directing light onto the substrate 122, having an oxide layer 124 and the particles 126 to be detected, and an imaging system 130 for capturing images of the light reflected by the substrate 122, the oxide layer 124 and the particles 126. The system 100 can also include a computer system 140 for controlling the illumination source 101 and receiving imaging signals from the imaging system 130. In a preferred embodiment, the illumination source 101 includes incoherent light source (LED) 102 that provides incoherent light in one wavelength having a substantially narrow band of wavelengths. In some embodiments, the illumination source 101 can include three or more incoherent light sources 102, 104, 106 that produce incoherent light in three different wavelengths. The Light Emitting Diodes (LEDs) or equivalent light sources, each provide incoherent light at one of the plurality of wavelengths. In some embodiments, the illumination source 101 can include an array of illumination elements, including one or more illumination elements providing light at the same wavelength and being arranged in a geometric (e.g., circular or rectangular), random, or spatially displaced array. The light from the illumination source 101 can be directed through a focusing lens 112 and other optical elements (e.g., polarizing lens, filters and light conditioning components, not shown) to a beam splitter 114 that directs the light onto the substrate 122, the oxide layer 124 and the particles 126. Optical components can be provided to condition the light to uniformly illuminate substantially the entire surface of the layered substrate 122. The light reflected by the substrate 122, the oxide layer 124 and the particles 126 can be directed through the beam splitter 114 and imaging lens 134 into a camera 132 to capture images of the substrate surface. The camera 132 can be, for example, a CCD camera (color or monochromatic) and produce image signals representative of the image. The image signals can be sent from the camera 132 to the computer system 140 either by a wireless or wired connection.

Computer system 140 can include one or more central processing units (CPUs) and associated memory (including volatile and non-volatile memory, such as, RAM, ROM, flash, optical and magnetic memory) and a display 146 for presenting information to a user. The memory can store one or more computer programs that can be executed by the CPUs to store and process the image data and produce images of the substrate surface. Additional computer programs can be provided for analyzing the image data and the images to detect interference patterns and the particles 126 on the surface of the oxide layer 124 of the substrate 122.

The computer programs can be executed by the computer to implement a method according to one or more embodiments of the present invention whereby interferometric measurements can be made. The computer programs can control the illumination source 101 comprising one (or more) LED that can be used to illuminate layered substrate. The optical path difference (OPD) between the bottom and top surface causes an interference pattern. The interference patterns can be imaged as intensity variations by the CCD camera 132 across the whole substrate at once.

In an alternative embodiment, each incoherent light source can be an optical fiber (not shown) that directs the light at the layered substrate 122. Optical components can be provided to condition the light to uniformly illuminate substantially the entire surface of the layered substrate 122

Figure 2:
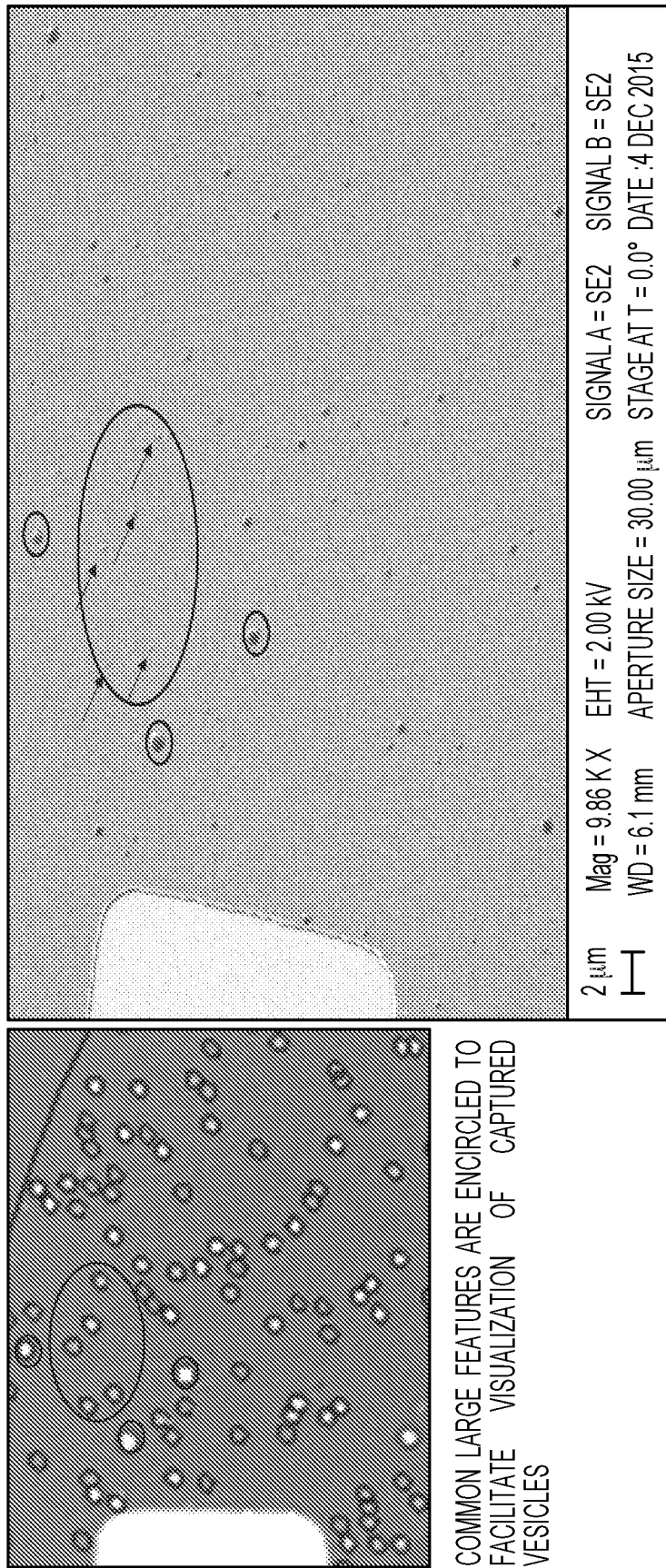
FIG. 2 shows detection of GPC1 exosomes directly from plasma with the imaging platform according to this disclosure in a side-by-side comparison of detection of the same sample with a scanning electron microscope, according to an illustrative embodiment of the invention.

FIGS. 2A-2B shows detection of GPC1 exosomes directly from plasma with the imaging platform according to this disclosure in a side-by-side comparison of detection of the same sample with a scanning electron microscope. As can be seen in FIG. 2A, the incubated PDAC patient sample was imaged with the sensor platform disclosed herein and the sample was then stained with Osmium Tetroxide (lipid specific stain) to visualize the sample with an Electron Microscope as shown in FIG. 2B. The incubated PDAC patient sample was imaged with the sensor platform was cropped as shown in FIG. 2A to allow visualization of a similar area to the image from the electron microscope in FIG. 2B. As can be seen from the side-by-side comparison, common large features from the sample are highlighted in red to facilitate comparison between the imaged samples, and the green circles show some of the imaged small nanoparticles.

Figure 3:
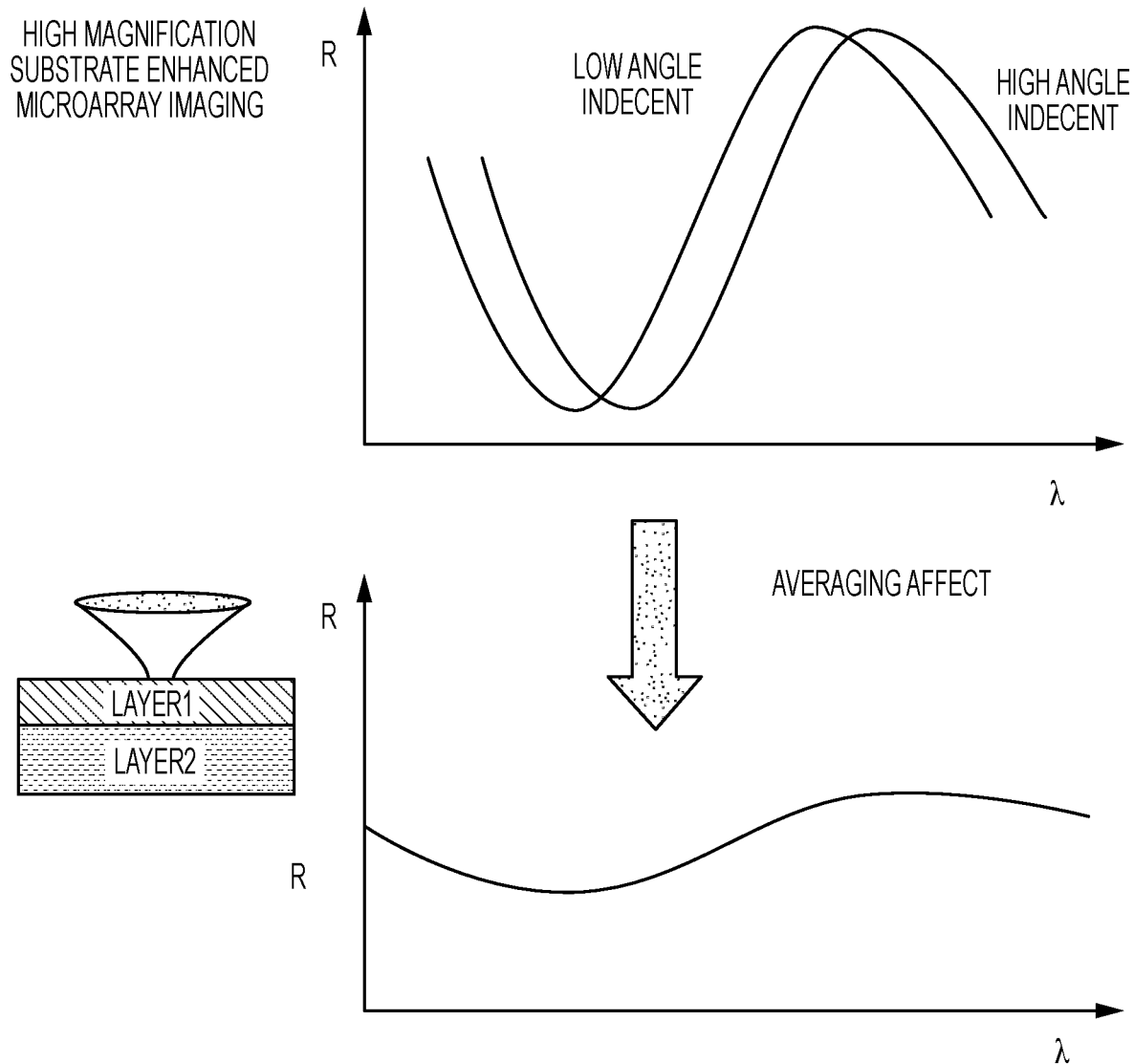
FIG. 3 illustrates some properties desired for performing high magnification substrate enhanced microarray imaging, according to an illustrative embodiment of the invention.

FIG. 3 demonstrates the properties desired for performing high magnification substrate enhanced microarray imaging. For making high magnification imaging, objectives with higher numerical apertures (NA) should be used. Because the light is collected at a high range of angles, most of the light averages out (as illustrated in the figure). Also the use of thin oxide increases the limit for spatial resolution because of less dispersion in light as it passes through it.

Figure 4:
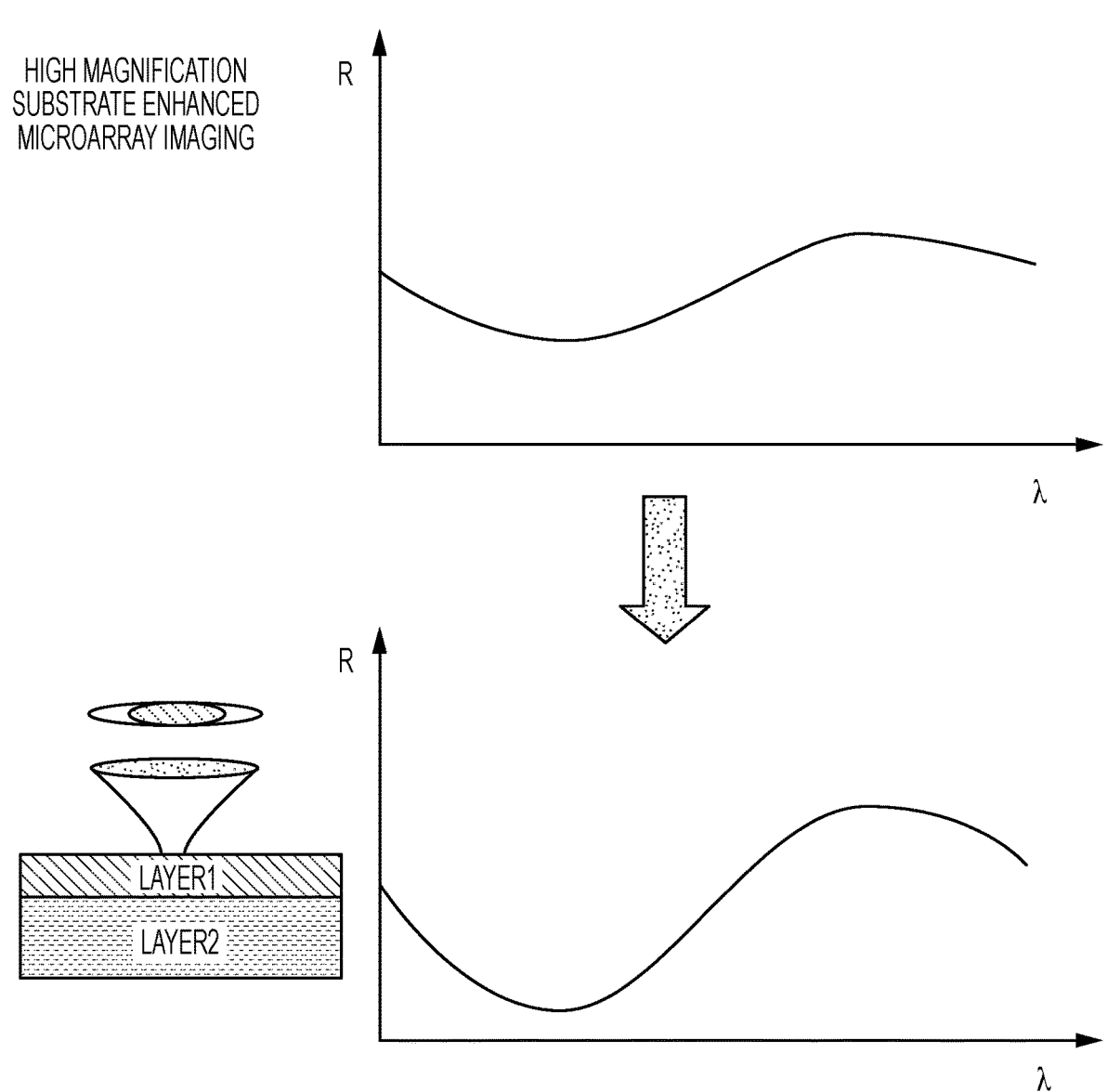
FIG. 4 depicts using a spatial filter as an option for performing high magnification substrate enhanced microarray imaging, according to an illustrative embodiment of the invention.

FIG. 4 depicts using a spatial filter as an option for performing high magnification substrate enhanced microarray imaging. To maintain the lateral resolution for single particle detection and the contrast of the reflectivity curve, it may be desirable to place a spatial filter on the collection path that will reject a range of angles of the reflected light. Simple observation of interference can be seen on the colors on soap bubbles. One of the ultimate examples of high precision measurements using optical interference is the LIGO with attometer capability.

Figure 5:
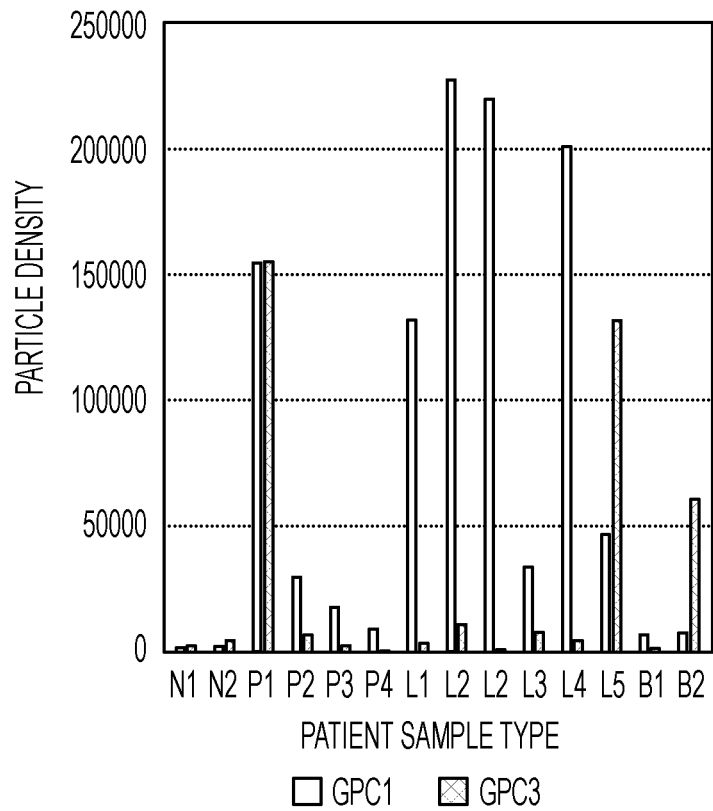
FIG. 5 depicts the surface expression of glypican-1 and glypican-3 on exosomes in plasma obtained from cancer patients (pancreatic, lung, or breast cancer patients)

FIG. 5 depicts the surface expression of glypican-1 and glypican-3 on exosomes in plasma obtained from cancer patients (pancreatic, lung, or breast cancer patients). The measurement was made using the spectral reflectance imaging technique for counting of glypican-1 and glypican-3 expressing exosomes from human plasma. The data shows higher expression of glypican-1 and/or glypican-3 in cancer patients.

Figure 6:
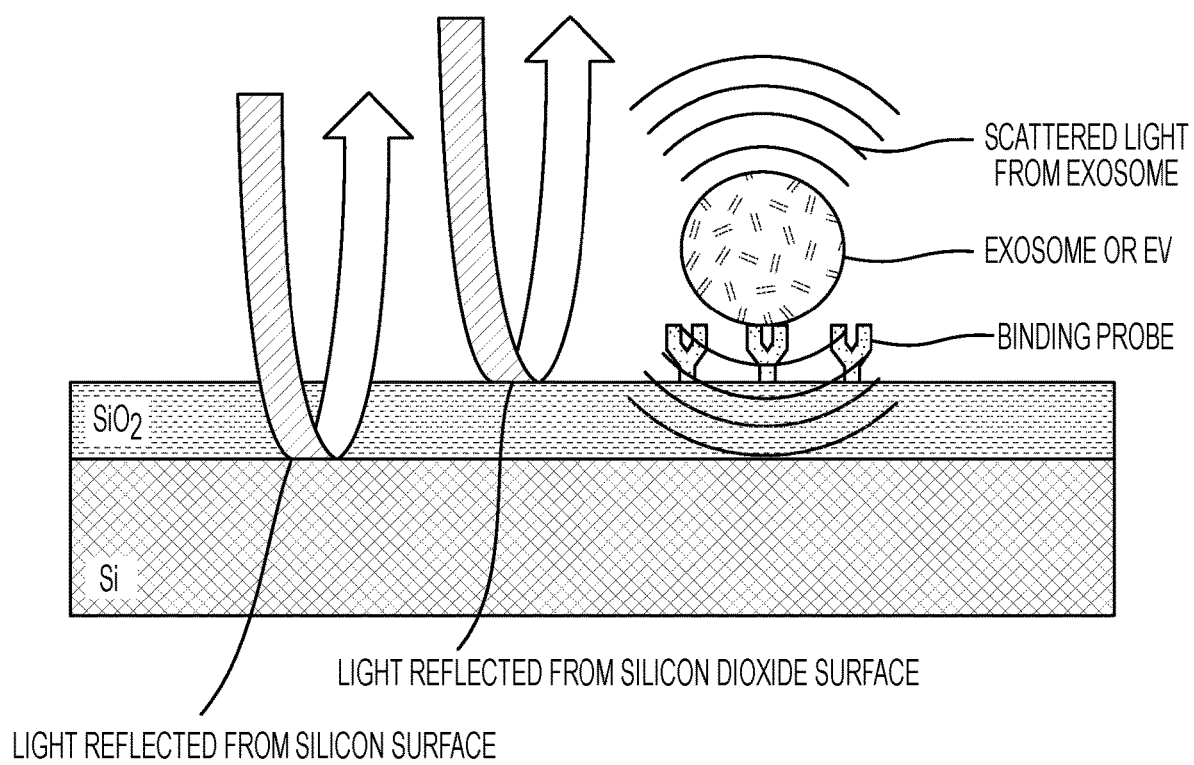
FIG. 6 illustrates a schematic of a substrate functionalized with a binding probe and how light illuminating the substrate is spectrally reflected from the two layers of the substrate, which interferes with the scattered light from particle(s) bound to the one substrate surface.

FIG. 6 depicts the interferometric scattering of reflected light upon absorption of nanoparticle extracellular vesicles such as exosomes to binding agents on a surface of a substrate. The reflections from the different layers including the Silicon surface and the Silicon dioxide surface interfere with the light reflected from the nanoparticles captured by the binding agents cause a change in the reflected light, which can be detected by the image processing system. In particular, a reflectance signature of the incident light is altered by said nanoparticles on a binding layer on the substrate surface to interfere with the light reflected from the Silicon surface and the Silicon Dioxide surface. The imaging system of FIG. 1 detects the interference in the reflection from the extracellular vesicles as compared to reflective properties of the Silicon surface and the Silicon Dioxide and an image processing system comprises a forward model to provide accurate and quantitative sizing of the extracellular vesicles. A preferred embodiment of the imaging device uses a single wavelength (band) of light to measure the interference/mixing of reflected light from the binding layer with the scattered light from the particle (scattering of the light).

Figure 7A:
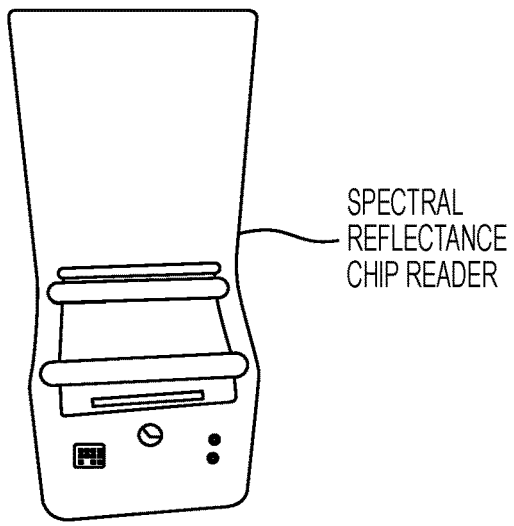
FIG. 7A is a picture of the instrument for the imaging of the substrate, according to an illustrative embodiment of the invention.
Figure 7B:
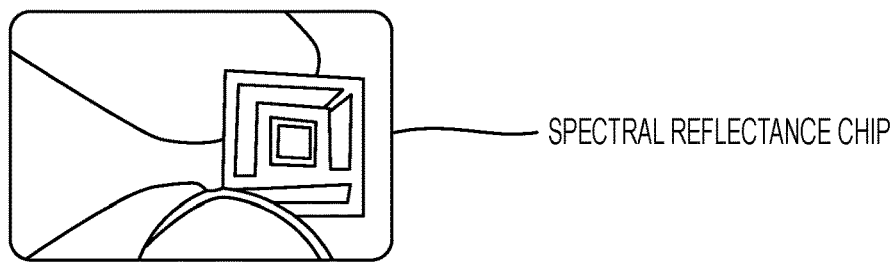
FIG. 7B is an image of a spectral reflectance chip (substrate), according to an illustrative embodiment of the invention.
Figure 7C:
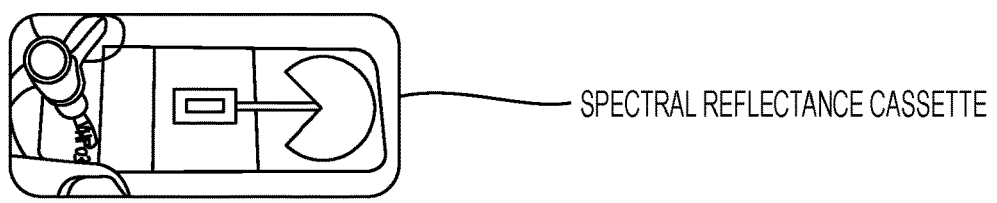
FIG. 7C is an image of the spectral reflectance chip disposed within a microfluidic cassette, which allows flowing of a sample over the substrate, according to an illustrative embodiment of the invention.
Figure 7D:
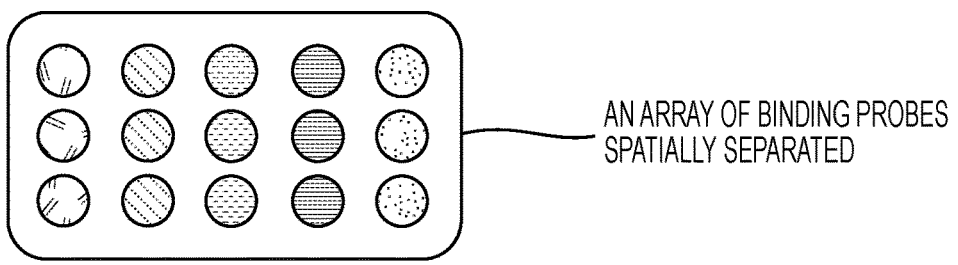
FIG. 7D is an illustration of an array of binding probes on substrate, according to an illustrative embodiment of the invention.

FIG. 7A is a picture of the instrument for the imaging of the substrate, as described herein. FIG. 7B is an image of a spectral reflectance chip (substrate), as been described herein. FIG. 7C is an image of the spectral reflectance chip disposed within a microfluidic cassette, which allows flowing of a sample over the substrate. FIG. 7D is an illustration of an array of binding probes on substrate, as described herein.

Figure 8A:
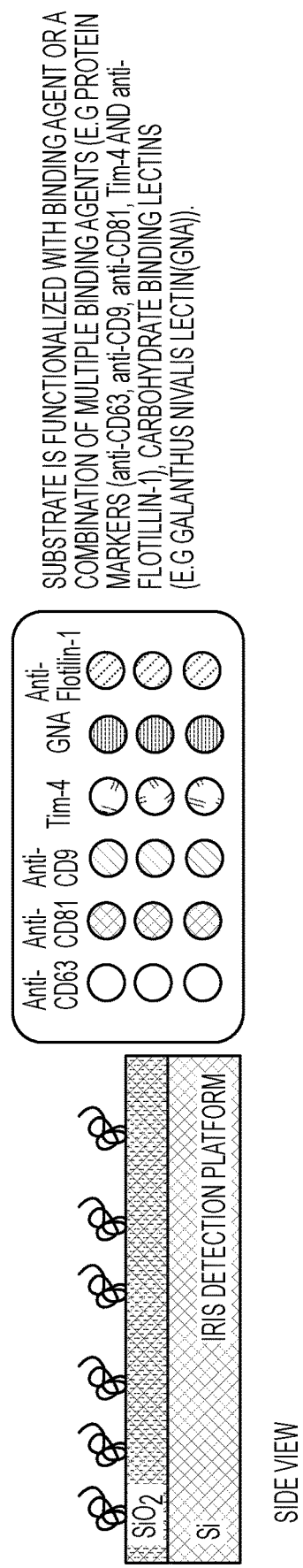
FIGS. 8A-8C show a schematic depicting that extracellular vesicles such as exosomes can be isolated on a sensor chip through physical absorption or binding agents, according to illustrative embodiments of the invention. For example, binding agents can target bioparticle surface charge, glycosylation, lipid composition, and/or surface protein.
Figure 8B:
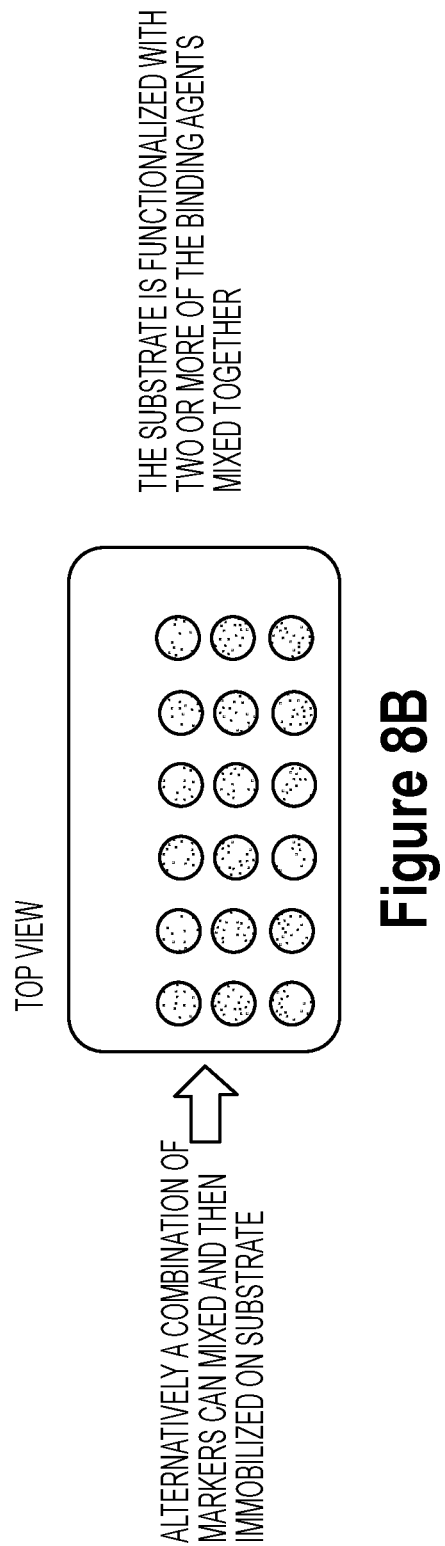
Figure 8C:
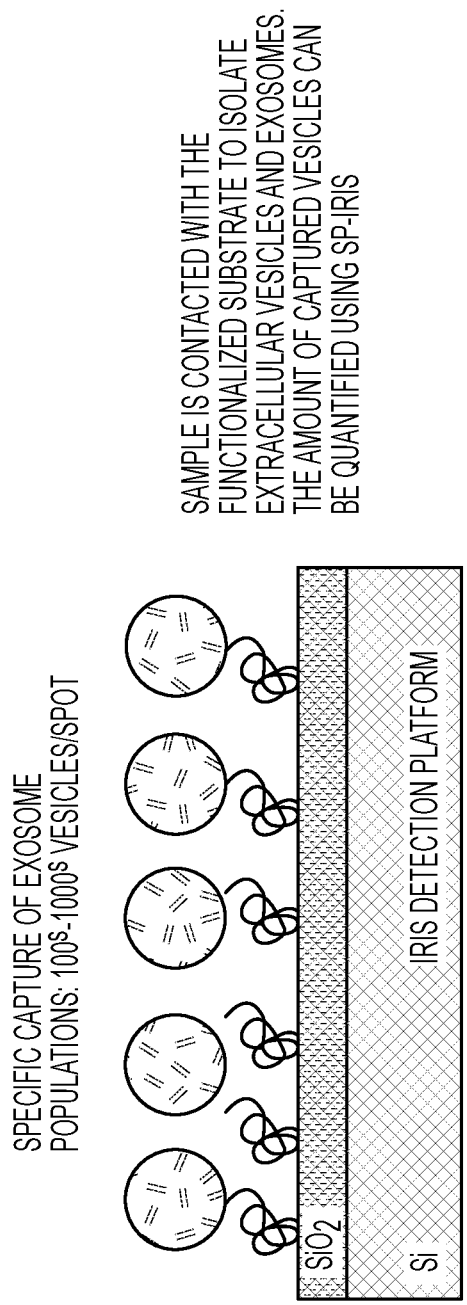

FIGS. 8A-8C show a schematic depicting that extracellular vesicles such as exosomes can be isolated on a sensor chip through physical absorption or binding agents, according to illustrative embodiments of the invention. For example, binding agents can target bioparticle surface charge, glycosylation, lipid composition, and/or surface protein.

FIG. 8A shows a schematic of a substrate that is functionalized with a binding agent or a combination of multiple binding agents (e.g., protein markers such as anti-CD63, anti-CD9, anti-CD81, Tim-4 and anti-flotillin-1; e.g., carbohydrate binding lectins such as *Galanthus nivalis* lectin (GNA)), according to an illustrative embodiment on the invention.

FIG. 8B shows alternatively to the schematic depicted in FIG. 8A, a combination of markers can be mixed and then immobilized on a substrate. The substrate is functionalized with two or more binding agents that are mixed together.

FIG. 8C shows a schematic where a sample is contacted with the functionalized substrate to isolate extracellular vesicles and exosomes, according to an illustrative embodiment of the invention. The amount of captured vesicles can be quantified using an interferometric biosensing (e.g., SP-IRIS).

Figure 9:
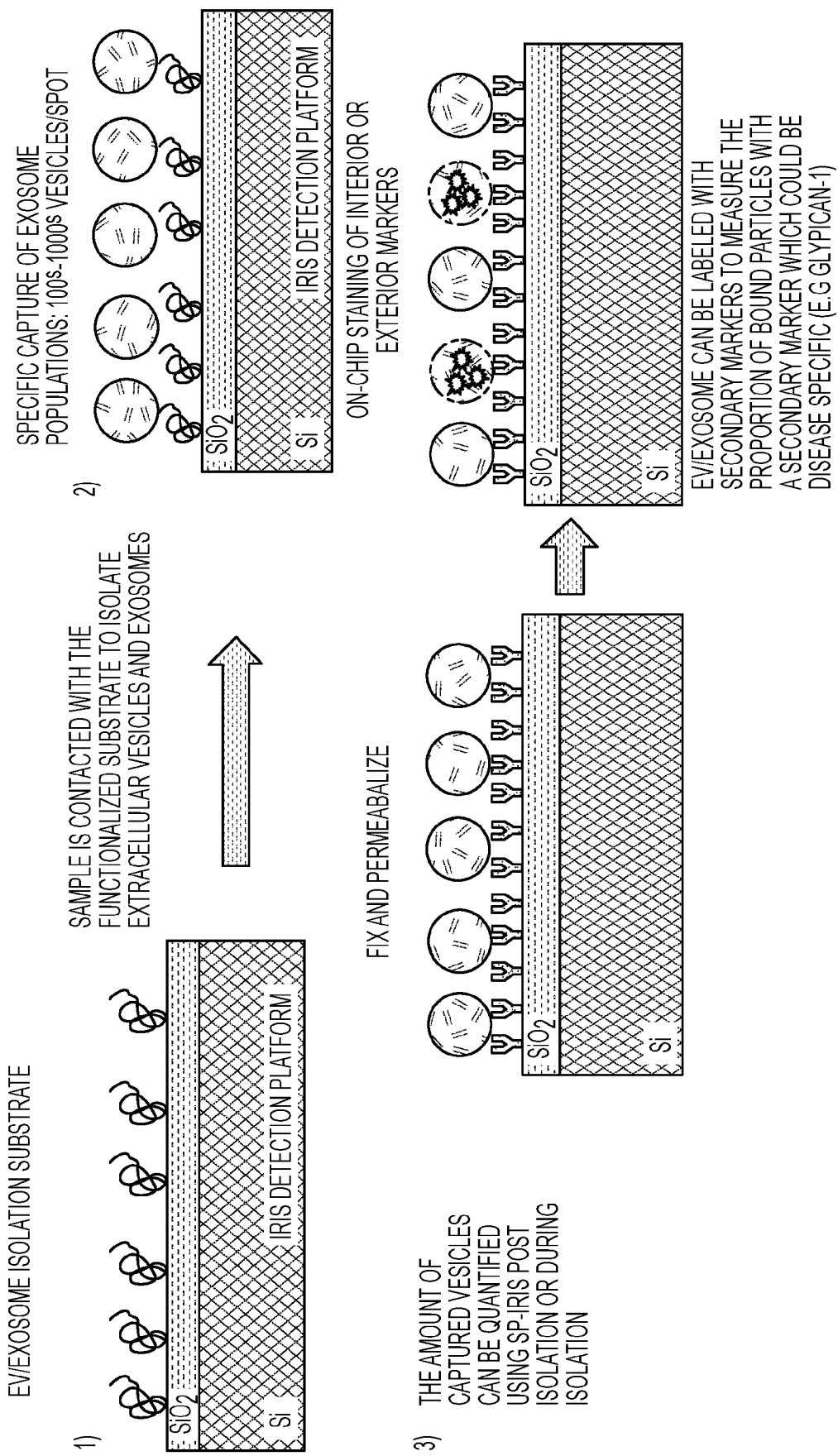
FIG. 9 shows a schematic of a method of isolation of extracellular vesicles (e.g., exosomes) on a substrate, according to an illustrative embodiment of the invention. A sample is contacted with a functionalized substrate to isolate extracellular vesicles and/or exosomes. The amount of captured vesicles can be quantified using SP-IRIS post isolation or during isolation. The substrate containing the captured extracellular vesicles and/or exosomes is fixed and permeabilized. Captured extracellular vesicles and/or exosomes can be labeled with secondary markers to measure the proportion of bound particles with a secondary marker which could be disease specific (e.g., glypican-1).

FIG. 9 shows a schematic of a method of isolation of extracellular vesicles (e.g, exosomes) on a substrate, according to an illustrative embodiment of the invention. A sample is contacted with a functionalized substrate to isolate extracellular vesicles and/or exosomes. The amount of captured vesicles can be quantified using SP-IRIS post isolation or during isolation.

The substrate containing the captured extracellular vesicles and/or exosomes is fixed and permeabilized. Captured extracellular vesicles and/or exosomes can be labeled with secondary markers to measure the proportion of bound particles with a secondary marker which could be disease specific (e.g., glypican-1).

Figure 10:
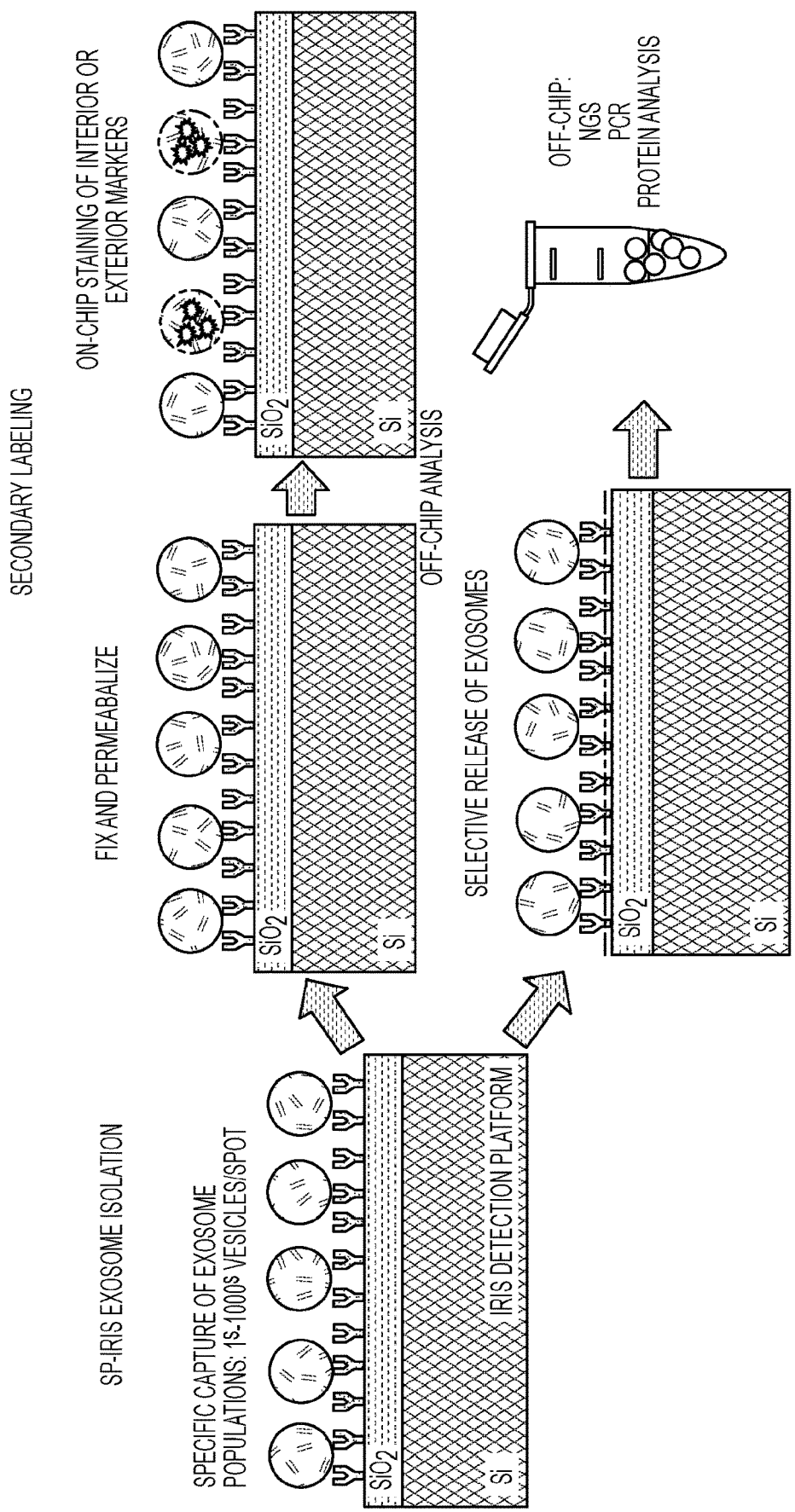
FIG. 10 shows a schematic of a method of isolation of extracellular vesicles (e.g., exosomes) on a substrate, according to an illustrative embodiment of the invention.

FIG. 10 shows a schematic of a method of isolation of extracellular vesicles (e.g., exosomes) on a substrate, according to an illustrative embodiment of the invention.

Figure 11:
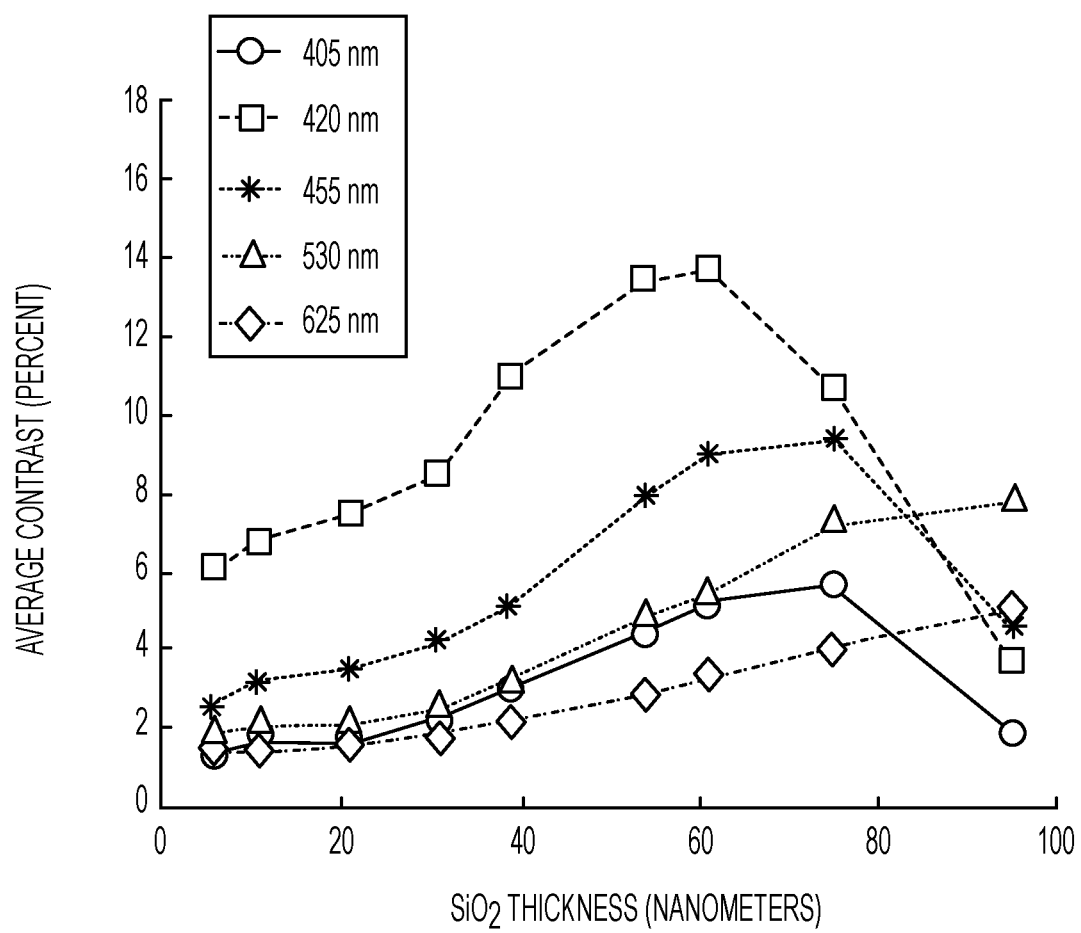
FIG. 11 shows signal in percent contrast from 100 nm diameter polystyrene beads adsorbed to a SP-IRIS substrate which comprises a silicon with semi-transparent silicon dioxide top layer. The nanoparticles are adsorbed to the silicon dioxide top layer. The percent contrast is shown for different oxide thickness and wavelength of illumination.

FIG. 11 shows signal in percent contrast from 100 nm diameter polystyrene beads adsorbed to a SP-IRIS substrate which comprises a silicon with semi-transparent silicon dioxide top layer. The nanoparticles are adsorbed to the silicon dioxide top layer. The percent contrast is shown for different oxide thickness and wavelength of illumination.

Figure 12:
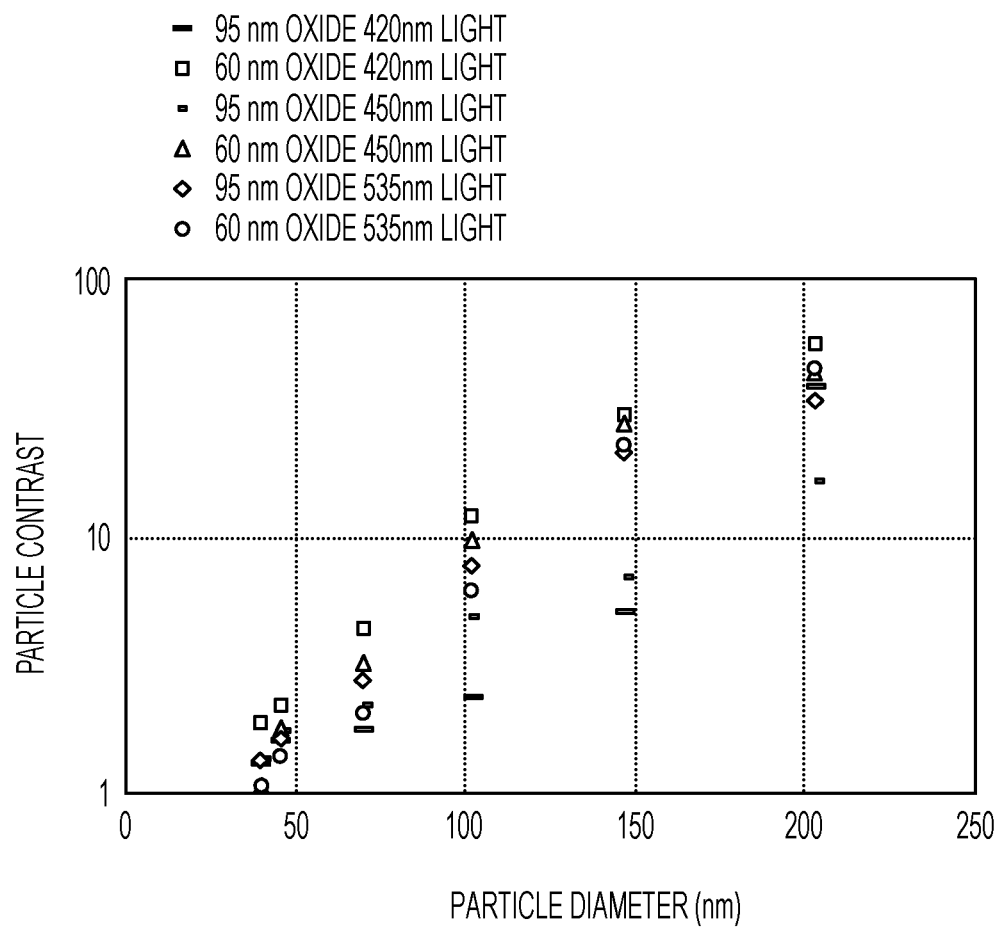
FIG. 12 shows signal in percent contrast for a range of nanoparticle diameters from 40 to 220 nanometers. The particle contrast is plotted for different oxide thickness and illumination wavelength.
Figure 13:
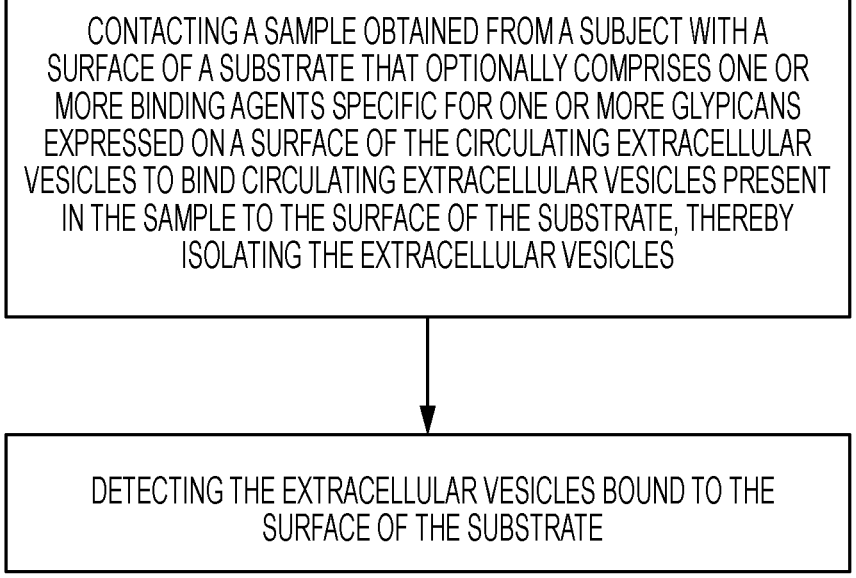
FIGS. 13 and 14 show a method of isolating cancer-derived circulating extracellular vesicles (e.g., exosomes), according to an illustrative embodiment of the invention.
Figure 14:
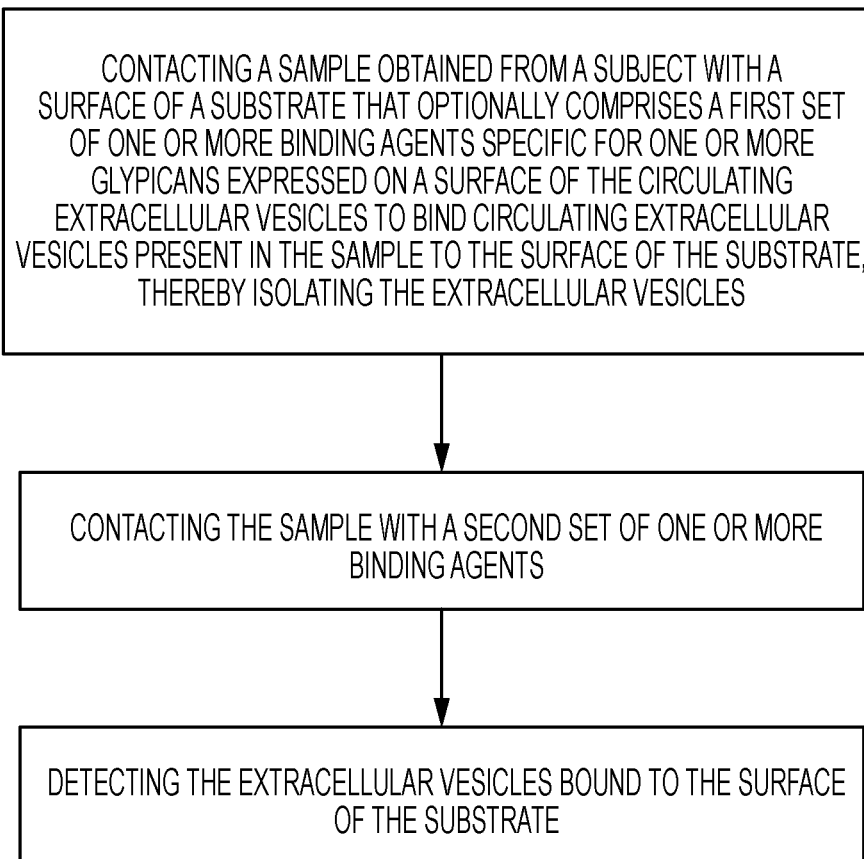
Figure 15:
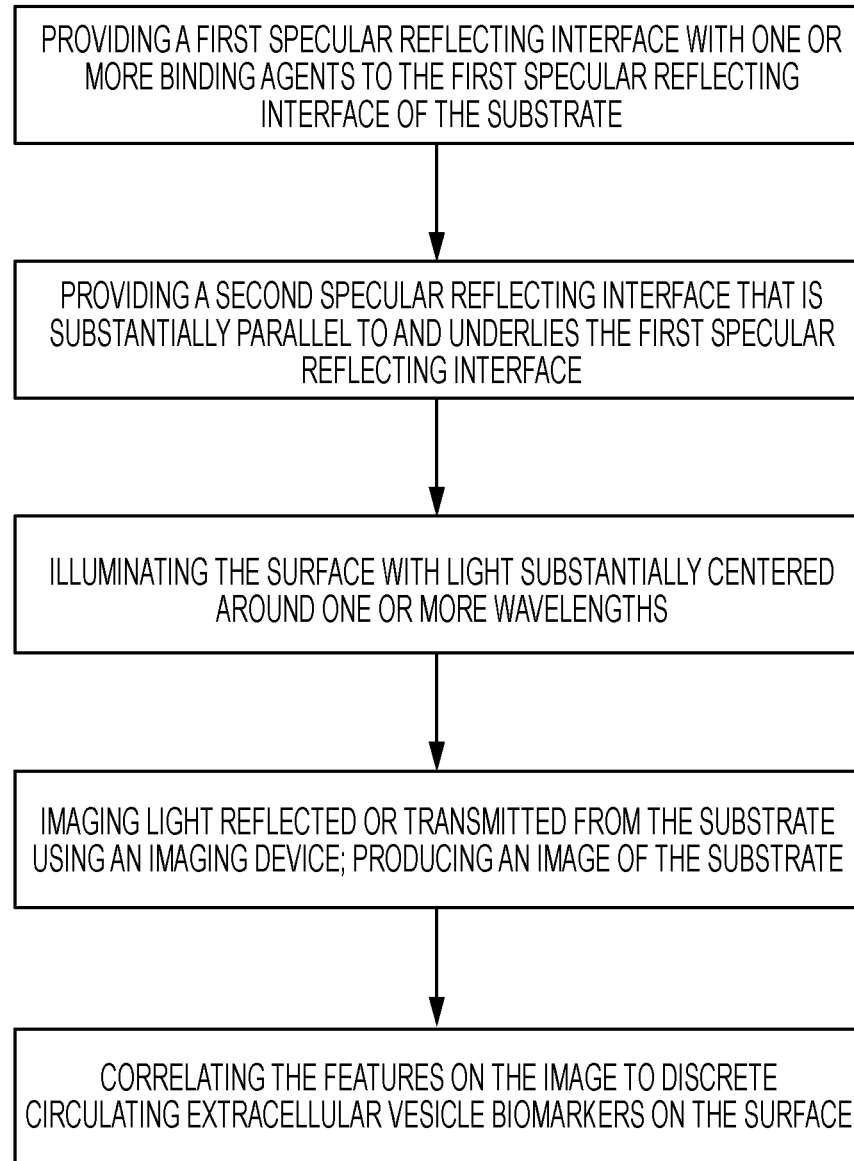
FIG. 15 shows a method for detecting the binding of a circulating extracellular vesicle (e.g., exosomes) to a surface of a substrate, according to an illustrative embodiment of the invention.

FIG. 12 shows signal in percent contrast for a range of nanoparticle diameters from 40 to 220 nanometers. The particle contrast is plotted for different oxide thickness and illumination wavelength.

In some embodiments three or more LEDs with different emission peak wavelengths can be used as the light source. In some embodiments where more than one incoherent light source is used, the light sources used have a narrow range of wavelength, and the width between the wavelengths of each individual light source is small. In some embodiments, one or two light sources are used.

In some embodiments described herein, the microarray or binding agent is fabricated on a layered substrate comprising anywhere from a few nanometers to 100 nm of $SiO_2$ layered on a Si wafer. In some embodiments, the microarray or binding agent is fabricated on a layered substrate comprising 95-100 nm of $SiO_2$ layered on a Si wafer. In some embodiments, the microarray or binding agent is fabricated on a layered substrate comprising 30-60 nm of $SiO_2$ layered on a Si wafer. A preferred embodiment includes a green LED light source (near 535 nm) and 100 nm oxide of $SiO_2$ layered on a Si wafer. A second preferred embodiment includes an ultraviolet LED light source (near 420 nm) and 60 nm oxide of $SiO_2$ layered on a Si wafer. A third preferred embodiment, for use when imaging in complex media, includes an ultraviolet LED light source (near 420 nm) and 30-to-60 nm oxide of $SiO_2$ layered on a Si wafer. The devices and methods described herein, can be used, in part, for high magnification interferometric measurements, for example, but not limited to, detecting extracellular vesicles, such as an exosome biomarker for a cancer, in a given sample.

A "particle," as defined herein, refers to any target to be detected by the devices and methods described herein that has a radius from a few nanometers up to a few microns.

The use of high-magnification interferometric measurements is an approach to detection of biomolecular targets and particles. The methods and devices described herein provide for imaging through a high magnification objective lens with a high numerical aperture and placing a spatial filter on the camera's optical axis. The high numerical aperture objective lens will allow imaging at high magnifications and the spatial filter is used to maintain the contrast of the interference cause by the layered substrate by only collecting light from a high angle or a range of angles of incident light. The optical setup described will allow for detection of sub-wavelength structures without losing contrast or lateral resolution.

Another approach to simplifying the imaging device described herein can be to use a broadband source and a colored CCD camera in which the spectral sampling is done by the camera. Pixels of the camera dedicated for detection of separate colors can be used to extract the intensity of light included in a given spectral band, thus enable a spectral detection scheme.

One advantage to the embodiments with an LED light source is that an LED based illumination source allows the imaging device to be more robust and portable, thus allowing field applications. Another advantage is the high magnification capability of the invention. High magnification will allow for the detection of single biomolecular targets on the binding agent surface (e.g., >a few nm in length or diameter). In some embodiments, a white light source or an RGB LED with a 3CCD or other color camera can be used to capture spectral information at three distinct wavelengths to increase temporal resolution. This is beneficial in studying dynamic biological interactions, for example.

The device described herein facilitates a method of using an LED illumination source for substrate enhanced detection of extracellular vesicles such as exosome biomarkers in a sample bound to a surface. The device provides in one aspect a high-throughput spectroscopy method for simultaneously recording a response of an entire substrate surface. The device and methods can be used in any high-throughput application. One aspect of the invention thus provides a platform or a system for high-throughput optical sensing of solid substrates, comprising an illuminating source and an imaging device.

In some embodiments the imaging device is a camera. The device can be used for multiplexed and dynamic detection of extracellular vesicles, such as exosome biomarkers on a substrate.

All embodiments of the device can be described as functional modules, which include computer executable instructions recorded on computer readable media and which cause a computer to perform method steps when executed. The modules can be segregated by function for the sake of clarity. However, it should be understood that the modules need not correspond to discrete blocks of code and the described functions can be carried out by the execution of various code portions stored on various media and executed at various times.

In some embodiments, the device provides a system for obtaining data regarding optical sensing of a solid substrate comprising a) a determination module configured to determine optical information, wherein the optical information comprises sampling a least one wavelength using a narrow band light source; b) a storage device configured to store data output from the determination module; c) a comparison module adapted to compare the data stored on the storage device with a control data, the comparison being a retrieved content; and d) a display module for displaying a page of the retrieved content for the user on the client computer, wherein the retrieved content is a light absorption profile of the substrate, wherein a certain light absorption profile is indicative of binding of an exosome biomarker.

In some embodiments, the invention provides a computer program comprising a computer readable media or memory having computer readable instructions recorded thereon to define software modules including a determination module and a comparison module for implementing a method on a computer, said method comprising a) determining with the determination module optical information, wherein the optical information comprises sampling at least one wavelength using a narrow-band light source; b) storing data output from the determination module; c) comparing with the comparison module the data stored on the storage device with a control data, the comparison being a retrieved content, and d) displaying a page of the retrieved content for the user on the client computer, wherein the retrieved content is a light absorption profile of the solid substrate, wherein a certain light absorption profile is indicative of binding of an exosome biomarker.

The "computer readable medium" can include data and computer-executable instructions for performing the steps of the method of the invention. Suitable computer readable media include floppy disk, CD-ROM/DVD/DVD-ROM, hard-disk drive, flash memory, ROM/RAM, magnetic tapes and etc. The computer executable instructions can be written in a suitable computer language or combination of several languages. Basic computational biology methods are described in, e.g. Setubal and Meidanis et al.

Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., $2^{nd}$ ed., 2001).

In some aspects, the function modules of embodiments of the device include a determination module, a storage device, a comparison module and a display module. The determination module can include computer executable instructions to determine and provide optical information using an optical instrument. As used herein, an "optical instrument" refers to any instrument that either processes light waves to enhance an image for viewing, or analyzes light waves (or photons) to determine one of a number of characteristic optical properties.

Known determination modules for determining optical properties include, for example, but are not limited to, microscopes, cameras, interferometers (for measuring the interference properties of light waves), photometers (for measuring light intensity); polarimeters (for measuring dispersion or rotation of polarized light), reflectometers (for measuring the reflectivity of a surface or object), refractometers (for measuring refractive index of various materials), spectrometers or monochromators (for generating or measuring a portion of the optical spectrum, for the purpose of chemical or material analysis), autocollimators (used to measure angular deflections), and vertometers (used to determine refractive power of lenses such as glasses, contact lenses and magnifier lens).

A "spectrograph" or "spectrometer", as defined herein, is an optical instrument used to measure properties of light over a specific portion of the electromagnetic spectrum, typically used in spectroscopic analysis to identify materials. The variable measured is most often the light's intensity but could also, for instance, be the polarization state. The independent variable is usually the wavelength of the light, normally expressed as a fraction of a meter, but sometimes expressed as a unit directly proportional to the photon energy, such as wavenumber or electron volts, which has a reciprocal relationship to wavelength. A spectrometer is used in spectroscopy for producing spectral lines and measuring their wavelengths and intensities. Spectrometer is a term that is applied to instruments that operate over a very wide range of wavelengths, from gamma rays and X-rays into the far infrared. If the region of interest is restricted to near the visible spectrum, the study is called spectrophotometry.

Spectrophotometry involves the use of a spectrophotometer. As defined herein, a "spectrophotometer" is a photometer (a device for measuring light intensity) that can measure intensity as a function of the color, or more specifically, the wavelength of light. There are many kinds of spectrophotometers. Among the most important distinctions used to classify them are the wavelengths they work with, the measurement techniques they use, how they acquire a spectrum, and the sources of intensity variation they are designed to measure. Other important features of spectrophotometers include the spectral bandwidth and linear range. There are two major classes of spectrophotometers; single beam and double beam. A double beam spectrophotometer measures the ratio of the light intensity on two different light paths, and a single beam spectrophotometer measures the absolute light intensity. Although ratio measurements are easier, and generally more stable, single beam instruments have advantages; for instance, they can have a larger dynamic range, and they can be more compact. Historically, spectrophotometers use a monochromator to analyze the spectrum, but there are also spectrophotometers that use arrays of photosensors. Especially for infrared spectrophotometers, there are spectrophotometers that use a Fourier transform technique to acquire the spectral information quicker in a technique called Fourier Transform InfraRed. The spectrophotometer quantitatively substance). The most common application of spectrophotometers is the measurement of light absorption, but they can be designed to measure diffuse or specular reflectance. Strictly, even the emission half of a luminescence instrument is a kind of spectrophotometer.

The optical information determined in the determination module can be saved to and read by the storage device. As used herein the "storage device" is intended to include any suitable computing or processing apparatus or other device configured or adapted for storing data or information.

Examples of storage devices suitable for use with the present invention include stand-alone computing apparatus; communications networks, including local area networks (LAN), wide area networks (WAN), Internet, Intranet, and Extranet; and local and distributed processing systems including the "cloud." Storage devices also include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded there on sequence information or expression level information. The data is typically provided in digital form that can be transmitted and read electronically, e.g., via the Internet, on diskette, or any other mode of electronic or non-electronic communication.

As used herein, "stored" refers to a process for storing information on the storage device such that it can be read back from the device. Those skilled in the art can readily adopt any of the presently known methods for recording information on known media to generate manufactures comprising the sequence information or expression level information.

A variety of software programs and formats can be used to store the optical information on the storage device. Any number of data processor structuring formats (e.g., text file or database) can be employed to obtain or create a medium having the information recorded thereon.

By providing optical information in computer-readable form, one can use the optical information in readable form to compare a specific optical profile with the optical information stored within a database of the comparison module. For example, direct comparison of the determined optical information from a given sample can be compared to the control data optical information (e.g., data obtained from a control sample). The comparison made in computer-readable form being the retrieved content from the comparison module, which can be processed by a variety of means.

The retrieved content can then be displayed through a "display module".

As used herein, a cassette is defined as configured to contain a silicon/silicon dioxide chip with a transparent and high-quality imaging window (COP or polycarbonate) with a thin channel of fluid.

As defined herein, a "light emitting diode (LED)" is an electronic light source based on the semiconductor diode. When the diode is forward biased (switched on), electrons are able to recombine with holes and energy is released in the form of light. This effect is called electroluminescence and the color of the light is determined by the energy gap of the semiconductor. The LED is usually small in area (less than 1 mm) with integrated optical components to shape its radiation pattern and assist in measures the fraction of light that passes through a given solution. In a spectrophotometer, a light from the lamp is guided through a monochromator, which picks light of one particular wavelength out of the continuous spectrum. This light passes through the sample that is being measured. After the sample, the intensity of the remaining light is measured with a photodiode or other light sensor, and the transmittance for this wavelength is then calculated. In short, the sequence of events in a spectrophotometer is as follows: the light source shines through the sample, the sample absorbs light, the detector detects how much light the sample has absorbed, the detector then converts how much light the sample absorbed into a number, the numbers are e are transmitted to a comparison module to be further manipulated (e.g. curve smoothing, baseline correction). Many spectrophotometers must be calibrated by a procedure known as "zeroing." The absorbency of some standard substance is set as a baseline value, so the absorbencies of all other substances are recorded relative to the initial "zeroed" substance. The spectrophotometer then displays % absorbency (the amount of light absorbed relative to the initial reflection. Like a normal diode, the LED consists of a chip of semiconducting material impregnated, or doped, with impurities to create a p-n junction. As in other diodes, current flows easily from the p-side, or anode, to the n-side, or cathode, but not in the reverse direction. Charge-carriers electrons and holes flow into the junction from electrodes with different voltages. When an electron meets a hole, it falls into a lower energy level, and releases energy in the form of a photon. The wavelength of the light emitted, and therefore its color, depends on the band gap energy of the materials forming the p-n junction. In silicon or germanium diodes, the electrons and holes recombine by a non-radiative transition which produces no optical emission, because these are indirect band gap materials. The materials used for the LED have a direct band gap with energies corresponding to near-infrared, visible or near-ultraviolet light. LEDs are usually built on an n-type substrate, with an electrode attached to the p-type layer deposited on its surface. P-type substrates, while less common, occur as well. Many commercial LEDs, especially GaN/InGaN, also use sapphire substrate. Most materials used for LED production have very high refractive indices. This means that much light will be reflected back in to the material at the material/air surface interface. LEDs of use for the present invention, include but are not limited to:

interfaces refer to those surfaces upon which incoming light undergoes "specular reflection," i.e., the mirror-like reflection of light (or sometimes other kinds of wave) from a surface, in which light from a single incoming direction (a ray) is reflected into a single outgoing direction. Such specular reflecting behavior of a surface, substrate or interface, is described by the law of reflection, which states that the direction of incoming light (the incident ray), and the direction of outgoing light reflected (the reflected ray) make the same angle with respect to the surface normal, thus the angle of incidence equals the angle of reflection; mathematically defined $\theta i=\theta r$. A second defining characteristic of specular reflection is that the incident, normal, and reflected directions are coplanar. Specular reflection can be accurately measured using, for example, a glossmeter. The measurement is based on the refractive index of an object. In some embodiments of the aspects described herein, a specular reflecting interface comprises a substrate having a transparent dielectric layer, for example a layer of Silicon Oxide ($SiO_2$) on a Silicon substrate. In some embodiments of aspects herein, the layer of Silicon Oxide ($SiO_2$) has a layer of binding agent for binding to nanoparticles such as an exosome biomarker thereon. In some embodiments, an alternative transparent dielectric layer, such as silicon nitride as well as other coatings can be used as a thin transparent or specular reflecting interface layer.

Applications of the Sensors and Methods

The ability to detect biological extracellular vesicles, e.g., exosomes, e.g., exosomes comprising an exosome biomarker, e.g., a cell surface biomarker, in a sample is fundamental to our understanding of both cell physiology and disease progression, as well as for use in various applica-

| Color | Wavelength [nm] | Voltage [V] | Semiconductor Material |
|---|---|---|---|
| Infrared | $\lambda > 760$ | $\Delta V < 1.9$ | Gallium arsenide (GaAs)<br>Aluminum gallium arsenide (AlGaAs) |
| Red | $610 < \lambda < 760$ | $1.63 < \Delta V < 2.03$ | Aluminum gallium arsenide (AlGaAs)<br>Gallium arsenide phosphide (GaAsP)<br>Aluminum gallium indium phosphide (AlGaInP)<br>Gallium(III) phosphide (GaP) |
| Orange | $590 < \lambda < 610$ | $2.03 < \Delta V < 2.10$ | Gallium arsenide phosphide (GaAsP)<br>Aluminum gallium indium phosphide (AlGaInP)<br>Gallium(III) phosphide (GaP) |
| Yellow | $570 < \lambda < 590$ | $2.10 < \Delta V < 2.18$ | Gallium arsenide phosphide (GaAsP)<br>Aluminum gallium indium phosphide (AlGaInP)<br>Gallium(III) phosphide (GaP) |
| Green | $500 < \lambda < 570$ | $2.18 < \Delta V < 4.0$ | Indium gallium nitride (InGaN)/Gallium(III) nitride (GaN)<br>Gallium(III) phosphide (GaP)<br>Aluminum gallium indium phosphide (AlGaInP)<br>Aluminum gallium phosphide (AlGaP) |
| Blue | $450 < \lambda < 500$ | $2.48 < \Delta V < 3.7$ | Zinc selenide (ZnSe)<br>Indium gallium nitride (InGaN)<br>Silicon carbide (SiC) as substrate<br>Silicon (Si) as substrate - (under development) |
| Violet | $400 < \lambda < 450$ | $2.76 < \Delta V < 4.0$ | Indium gallium nitride (InGaN) |
| Purple | multiple types | $2.48 < \Delta V < 3.7$ | Dual blue/red LEDs,<br>blue with red phosphor,<br>or white with purple plastic |
| Ultraviolet | $\lambda < 400$ | $3.1 < \Delta V < 4.4$ | diamond (C)<br>Aluminum nitride (AlN)<br>Aluminum gallium nitride (AlGaN)<br>Aluminum gallium indium nitride (AlGaInN) - (down to 210 nm) |
| White | Broad spectrum | $\Delta V = 3.5$ | Blue/UV diode with yellow phosphor |

As defined herein, a substrate surface can include a "specular reflecting interface." Such specular reflecting tions such as the early and rapid detection. Described herein are rapid, sensitive, simple to use, and inexpensive biosensors that are useful for a variety of applications involving the detection of nanoparticles, ranging from research and medical diagnostics, to detection of cancer.

Accordingly, in one aspect, the substrates described herein are used to detect binding of extracellular vesicles, e.g., exosomes, e.g., exosomes comprising an exosome biomarker, e.g., a cell surface biomarker, in a sample to a substrate layer, wherein binding of a exosome biomarkers present in a sample contacted with the substrate layer changes an optical path length relative to an optical path length in the absence of the sample, resulting in an interference pattern that is detected and measured by the device and methods described herein. In some embodiment, the sample that contacts the substrate can have a plurality of biomolecular targets, such that multiple extracellular vesicles bind to the substrate layer and are detected by the devices and methods described herein.

The devices and substrates can be used to study one or a number of specific binding interactions in parallel, i.e., multiplex applications. Binding of one or more specific extracellular vesicles in a sample to respective target surfaces can be detected. The substrate is illuminated with light, and if one or more nanoparticle targets in the sample binds one or more targets, they will appear in the image as single discrete objects allowing the detection of the individual binding of the nanoparticle targets. In embodiments where a biosensor substrate surface comprises an array of one or more distinct target locations comprising one or more specific targets, then the interference pattern is detected from each distinct location of the substrate.

Thus, in some embodiments, a variety of specific target molecules can be immobilized in an array format onto the substrate surface. The substrate is then contacted with a test sample of interest comprising potential nanoparticle targets, such as exosome biomarkers. Only the exosomes that specifically bind to the target surface are bound to the substrate. For high-throughput applications, biosensors can be arranged in an array of arrays, wherein several substrates comprising an array of specific binding molecules targets on the substrate surface are arranged in an array.

Accordingly, the devices and substrates are used to detect binding of one or more of a plurality of nanoparticle targets present in a sample to a biosensor substrate layer comprising one or more of a plurality of immobilized target molecules attached to the substrate layer. For example, one or more specific immobilized molecules can be arranged in an array of one or more distinct locations on the surface of the substrate layer. The one or more distinct locations can define microarray spots of about 50-500 microns, or about 150-200 microns in diameter.

A sample refers to any sample containing a biomolecular target, such as, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, prostatic fluid, or cellular lysates. A sample may also be obtained from an environmental source, such as water sample obtained from a polluted lake or other body of water, or a liquid sample obtained from a food source believed to contaminated.

As used herein the terms "sample" or "biological sample" means any sample, including, but not limited to cells, organisms, lysed cells, cellular extracts, nuclear extracts, components of cells or organisms, extracellular fluid, media in which cells are cultured, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears and prostatic fluid. In addition, a sample can be a viral or bacterial sample, a sample obtained from an environmental source, such as a body of polluted water, an air sample, or a soil sample, as well as a food industry sample.

The terms "label" or "tag", as used herein, refer to a composition capable of producing a detectable signal indicative of the presence of the target in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The articles "a" and "an" are used herein to refer to one or to more than one (i.e., at least one) of the grammatical object of the article. By way of example, "an element" means one element or more than one element. Thus, in this specification and the appended claims, the singular forms "a," "an," and "the" include plural references unless the context clearly dictates otherwise. Thus, for example, reference to a pharmaceutical composition comprising "an agent" includes reference to two or more agents.

As used herein, the term "comprising" means that other elements can also be present in addition to the defined elements presented. The use of "comprising" indicates inclusion rather than limitation. The term "consisting of" refers to compositions, methods, and respective components thereof as described herein, which are exclusive of any element not recited in that description of the embodiment. As used herein the term "consisting essentially of" refers to those elements required for a given embodiment. The term permits the presence of elements that do not materially affect the basic and novel or functional characteristic(s) of that embodiment of the invention. Other than in the operating examples, or where otherwise indicated, all numbers expressing quantities of ingredients or reaction conditions used herein should be understood as modified in all instances by the term "about." The term "about" when used in connection with percentages can mean +/−a percentage Exosomes Exosomes are small, membrane-bound vesicles with a size of 40-150 nm (Pan et al, 1985; Trams et al, 1981). They are secreted by many different cell types, such as cancer cells, mesenchymal cells, thrombocytes (Kahlert and Kalluri, Exosomes in tumor microenvironment influence cancer progression and metastasis. J. Mol Med. (Berl), 91:431-437, 2013; Heijnen et al, Activated platelets release two types of membrane vesicles: microvesicles by surface shedding and exosomes derived from exocytosis of multivesicular bodies and alpha-granules. Blood, 94:3791-3799, 1999; Raposo et al, B lymphocytes secrete antigen-presenting vesicles. The Journal of Experimental Medicine, 183: 1 161-1172, 1996), immune cells (Thery et al, Exosomes: composition, biogenesis and function. Nat. Rev. Immunol, 2:569-579, 2002), platelets (Janowska-Wieczorek et al, Microvesicles derived from activated platelets induce metastasis and angiogenesis in lung cancer. International Journal of Cancer, 1 13:752-760, 2005. Jazieh et al, The clinical utility of biomarkers in the management of pancreatic adenocarcinoma. Seminars in Radiation Oncology, 24:67-76, 2014), and endothelial cells (Hergenreider et al, Atheroprotective communication between endothelial cells and smooth muscle cells through miRNAs. Nature Cell Biology, 14:249-256, 2012). The first step in exosomes biogenesis involves the inward budding from the limiting membrane of late endosomes (Trajkovic et al, Ceramide triggers budding of exosome vesicles into multivesicular endosomes. Science, 319: 1244-1247, 2008). During this process, exosomes are packed with RNA molecules and proteins from the parental cell (Trams et al, Exfoliation of membrane ecto-enzymes in the form of micro-vesicles. Biochimica et Biophysica Acta, 645:63-70, 1981; Trajkovic Supra). After the release into the extracellular space, tumor-derived exosomes can transfer proteins and RNAs with oncogenic activity to recipient cells (Grange et al, Microvesicles released from human renal cancer stem cells stimulate angiogenesis and formation of lung premetastatic niche. Cancer Research, 71:5346-5356, 2011; Peinado et al, Melanoma exosomes educate bone marrow progenitor cells toward a pro-metastatic phenotype through MET. Nature Medicine, 18:883-891, 2012). Because exosomes are very stable under different conditions, they can protect their biological cargo against degradation and denaturation in the extracellular environment (Taylor and Gercel-Taylor, Exosomes/microvesicles: mediators of cancer-associated immunosuppressive microenvironments. Seminars in Immunopathology, 33:441-454, 2011). Genomic DNA in circulation is mainly contained in exosomes (Kahlert et al, Identification of double-stranded genomic DNA spanning all chromosomes with mutated KRAS and p53 DNA in the serum exosomes of patients with pancreatic cancer. The Journal of Biological Chemistry, 289:3869-3875, 2014). Exosomes from astrocytes and glioblastoma cells carry mitochondrial DNA (Guescini et al, C2C12 myoblasts release microvesicles containing mtDNA and proteins involved in signal transduction. Experimental Cell Research, 316: 1977-1984, 2010). Furthermore, it has been shown that exosomes from glioblastoma cell lines contain small amounts of single-stranded DNA as well as high levels of transposable elements (Balaj et al., Tumour microvesicles contain retrotransposon elements and amplified oncogene sequences. Nature Communications, 2: 180, 2011).

Exosomes are found in all body fluids of cancer patients, such as serum, saliva, cerebrospinal fluid, bone marrow aspirates, eye exudate/tears, and ascites (Peinado Supra; Lau et al, Role of Pancreatic Cancer-derived Exosomes in Salivary Biomarker Development. The Journal of Biological Chemistry, 288:26888-26897, 2013; Choi et al, Proteomic analysis of microvesicles derived from human colorectal cancer ascites. Proteomics, 1 1:2745-2751, 2011). As such, exosomes are promising diagnostic and predictive biomarkers in cancer. However, genetic profiling studies on circulating DNA from cancer patients are confounded by the fact that the isolated DNA represents all cells of the body, thus making mutation and genetic defects challenging (Murtaza et al, Non-invasive analysis of acquired resistance to cancer therapy by sequencing of plasma DNA. Nature, 497; 108-1 12, 2013; Yong, Cancer biomarkers: Written in blood. Nature, 51 1:524-526, 2014; Kirk, Breast cancer: Circulating tumour DNA the better of the blood biomarkers. Nature Reviews, Clinical Oncology, 10:247, 2013; Crowley et al, Liquid biopsy: monitoring cancer-genetics in the blood. Nature Reviews, Clinical Oncology, 10:472-484, 2013).

Several exosomes markers have been proposed and include members of the tetraspanin family (CD9, CD63, CD81), members of the endosomal sorting complexes required for transport (ESCRT; TSG101, Alix), and heat shock proteins (Hsp60, Hsp70, Hsp90) (Taylor and Gercel-Taylor, Supra). Epithelial tumor cells secrete exosomes carrying the epithelial cell adhesion molecule (EpCAM) (Taylor and Gercel-Taylor, Supra; Silva et al, Analysis of exosome release and its prognostic value in human colorectal cancer. Genes, Chromosomes & Cancer, 51:409-418, 2012; Runz et al., Malignant ascites-derived exosomes of ovarian carcinoma patients contain CD24 and EpCAM. Gynecologic Oncology, 107:563-571, 2007). Melanoma-derived exosomes contain the tumor-associated antigen Mart-1 and tyrosinase-related protein-2 (TYRP2) (Peinado, Supra; Mears et al, Proteomic analysis of melanoma-derived exosomes by two-dimensional polyacrylamide gel electrophoresis and mass spectrometry. Proteomics, 4:4019-4031, 2004; Andre et al, Malignant effusions and immunogenic tumour-derived exosomes. Lancet, 360:295-305, 2002). Exosomes from gastric cancer, breast cancer, and pancreatic cancer carry members of the human epidermal growth factor receptor (HER) family (Adamczyk et al, Characterization of soluble and exosomal forms of the EGFR released from pancreatic cancer cells. Life Sciences, 89:304-312, 2011; Baran et al, Circulating tumour-derived microvesicles in plasma of gastric cancer patients. Cancer Immunology, Immunotherapy: CII, 59:841-850, 2010; Ciravolo et al, Potential role of HER2-overexpressing exosomes in countering trastuzumab-based therapy. Journal of Cellular Physiology, 227:658-667, 2012).

The terms "microvesicle" and "exosome," as used herein, refer to a membranous particle, wherein at least part of the membrane of the exosomes is directly obtained from a cell. Most commonly, exosomes will have a size (average diameter) that is up to 5% of the size of the donor cell. Therefore, especially contemplated exosomes include those that are shed from a cell.

Exosomes may be detected in or isolated from any suitable sample type, such as, for example, body fluids. As used herein, the term "sample" refers to any sample suitable for the methods provided by the present invention. The sample may be any sample that includes exosomes suitable for detection or isolation. Sources of samples include blood, bone marrow, pleural fluid, peritoneal fluid, cerebrospinal fluid, urine, saliva, amniotic fluid, malignant ascites, broncho-alveolar lavage fluid, synovial fluid, breast milk, sweat, tears, joint fluid, and bronchial washes. In one aspect, the sample is a blood sample, including, for example, whole blood or any fraction or component thereof. A blood sample suitable for use with the present invention may be extracted from any source known that includes blood cells or components thereof, such as venous, arterial, peripheral, tissue, cord, and the like. For example, a sample may be obtained and processed using well-known and routine clinical methods (e.g., procedures for drawing and processing whole blood). In one aspect, an exemplary sample may be peripheral blood drawn from a subject with cancer.

Exosomes may also be isolated from tissue samples, such as surgical samples, biopsy samples, tissues, feces, and cultured cells. When isolating exosomes from tissue sources it may be necessary to homogenize the tissue in order to obtain a single cell suspension followed by lysis of the cells to release the exosomes. When isolating exosomes from tissue samples it is important to select homogenization and lysis procedures that do not result in disruption of the exosomes. Exosomes contemplated herein are preferably isolated from body fluid in a physiologically acceptable solution, for example, buffered saline, growth medium, various aqueous medium, etc.

Exosomes may be isolated from freshly collected samples or from samples that have been stored frozen or refrigerated. Although not necessary, higher purity exosomes may be obtained if fluid samples are clarified before precipitation with a volume-excluding polymer, to remove any debris from the sample. Methods of clarification include centrifugation, ultracentrifugation, filtration, or ultrafiltration. Most typically, exosomes can be isolated by numerous methods well-known in the art. One preferred method is differential centrifugation from body fluids or cell culture supernatants. Exemplary methods for isolation of exosomes are described in (Losche et al, Platelet-derived microvesicles transfer tissue factor to monocytes but not to neutrophils, Platelets, 15: 109-1 15, 2004; Mesri and Altieri, Endothelial cell activation by leukocyte microparticles, J. Immunol, 161: 4382-4387, 1998; Morel et al, Cellular microparticles: a disseminated storage pool of bioactive vascular effectors, Curr. Opin. Hematol, 1 1: 156-164, 2004). Alternatively, exosomes may also be isolated via flow cytometry as described in (Combes et al., A new flow cytometry method of platelet-derived microvesicle quantitation in plasma, Thromb. Haemost., 77:220, 1997).

One accepted protocol for isolation of exosomes includes ultracentrifugation, often in combination with sucrose density gradients or sucrose cushions to float the relatively low-density exosomes. Isolation of exosomes by sequential differential centrifugations is complicated by the possibility of overlapping size distributions with other microvesicles or macromolecular complexes. Furthermore, centrifugation may provide insufficient means to separate vesicles based on their sizes. However, sequential centrifugations, when combined with sucrose gradient ultracentrifugation, can provide high enrichment of exosomes.

Glypicans

Glypicans constitute one of the two major families of heparin sulfate proteoglycans, with the other major family being syndecans. Six glypicans have been identified in mammals, and are referred to as GPC1 through GPC6. While six glypicans have been identified in mammals, several characteristics remain consistent between these different proteins. First, the core protein of all glypicans is similar in size, approximately ranging between 60 and 70 kDa. Additionally, in terms of amino acid sequence, the location of fourteen cysteine residues is conserved. For all members of the glypican family, the C-terminus of the protein is attached to the cell membrane covalently via a glycosylphosphatidylinositol (GPI) anchor. To allow for the addition of the GPI anchor, glypicans have a hydrophobic domain at the C-terminus of the protein. Within 50 amino acids of this GPI anchor, the heparan sulfate chains attach to the protein core. Glypicans are critically involved in developmental morphogenesis, and have been implicated as regulators in several cell signaling pathways, including Wnt and Hedgehog. Abnormal expression of glypicans has been noted in multiple types of cancer, including ovarian cancer, mesothelioma, pancreatic cancer, glioma, and breast cancer.

Glypican-1 (also known as GLPC1 and Glypican Proteoglycan 1) is a cell surface heparan sulfate proteoglycan composed of a core protein anchored to the cytoplasmic membrane via a glycosyl phosphatidylinositol linkage. Isoform 1 (the canonical sequence) is 558 amino acids and 61.680 kDa (UniProtKB Protein Symbol: P35052-GPC1_HUMAN; Protein Accession: P35052). Glypican-1 has been associated with cancer-cell derived exosomes (WO2015085096; Melo et al. Glypican-1 identifies cancer exosomes and detects early pancreatic cancer (2015) Nature doi: 10.1038/nature14581). Glypican-2 or GPC2 is associated with diseases including mucopolysaccharidoses. The protein is 579 amino acids and 62830 Da(UniProtKB Protein Symbol: Q8N158-GPC2_HUMAN; Protein Accession: Q8N158). Glypican-3 (also known as GLPC3 and Glypican Proteoglycan 3) is a cell surface heparan sulfate proteoglycan composed of a core protein anchored to the cytoplasmic membrane via a glycosyl phosphatidylinositol linkage. Isoform 1 (the canonical sequence) is 580 amino acids and 65563 Da (UniProtKB Protein Symbol: P51654-GPC3_HUMAN; Protein Accession: P51654). Glypican-4 is 556 amino acids and 62412 Da (Protein Symbol: O75487-GPC4_HUMAN; Protein Accession: O75487). The GPC4 gene is adjacent to the 3' end of GPC3 and may also play a role in Simpson-Golabi-Behmel syndrome. Glypican-5 is 572 amino acids in length and 63707 Da (Protein Symbol: P78333-GPC5_HUMAN; Protein Accession: P78333). Glypican-6 is 555 amino acids in length and 62736 Da (Protein Symbol: Q9Y625-GPC6_HUMAN; Protein Accession: Q9Y625). Diseases associated with GPC6 include omodysplasia 1 and omodysplasia.

Antibodies

Antibodies can be used as binding agents, e.g., an anti-GLPC1 provided on a surface can be used to capture exosomes comprising GLPC1 or an anti-GLPC3 provided on a surface can be used to capture exosomes comprising GLPC3. As used herein, the term "antibody" or "antibody molecule" refers to immunoglobulin molecules and immunologically active portions of immunoglobulin (Ig) molecules, i.e., molecules that contain an antigen binding site that specifically binds, e.g., immunoreacts with, an antigen. By "specifically binds" or "immunoreacts with" is meant that the antibody reacts with one or more antigenic determinants of the desired antigen and has a lower affinity for other polypeptides, e.g., does not react with other polypeptides.

The term "antigen-binding site," or "binding portion" refers to the part of the immunoglobulin (Ig) molecule that participates in antigen binding. The antigen binding site is formed by amino acid residues of the N-terminal variable ("V") regions of the heavy ("H") and light ("L") chains. Three highly divergent stretches within the variable regions of the heavy and light chains, referred to as hypervariable regions, are interposed between more conserved flanking stretches known as "framework regions," or "FRs". The term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

The extent of the framework region and CDRs have been defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). Kabat definitions are used herein. Each VH and VL is typically composed of three CDRs and four FRs, arranged from amino-terminus to carboxy-terminus in the amino acid order: FR1, CDR1, FR2, CDR2, FR3, CDR3, FR4.

In embodiments, an antibody or antibody molecule encompasses full-length antibodies and antibody fragments. For example, a full-length antibody is an immunoglobulin (Ig) molecule (e.g., an IgG antibody) that is naturally occurring or formed by normal immunoglobulin gene fragment recombinatorial processes). In embodiments, an antibody or antibody molecule refers to an immunologically active, antigen-binding portion of an immunoglobulin molecule, such as an antibody fragment.

An antibody fragment, e.g., functional fragment, is a portion of an antibody, e.g., F(ab')$_2$, F(ab)$_2$, Fab', Fab, domain antibody (dAb), variable fragment (Fv), or single chain variable fragment (scFv). A functional antibody fragment binds with the same antigen that is recognized by the intact antibody. For example, an anti-insulin monoclonal antibody fragment binds to insulin. The term "antibody fragment" or "functional fragment" also includes isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Antibody fragments include functional fragments and are encompassed by the terms "antibody" or "antibody molecule."

Exemplary antibody molecules include full length antibodies and antibody fragments, e.g., dAb (domain antibody), single chain, Fab, Fab', and F(ab')$_2$ fragments, and single chain variable fragments (scFvs).

A scFv polypeptide molecule is a covalently linked variable heavy chain (VH)::variable light chain (VL) heterodimer, which can be expressed from a gene fusion including $V_H$ and $V_L$ encoding genes linked by a peptide-encoding linker. See, e.g., Huston et al. (1988) Proc Nat Acad Sci USA 85(16):5879-5883. The N- to C-terminal orientation of the VH and VL domains can be in either orientation, e.g., VH-VL or VL-VH. Large naïve human scFv libraries have been created to provide a source of rearranged antibody genes against a variety of target molecules. To isolate disease-specific antibodies, libraries can be constructed from individuals with certain diseases. See, e.g., Barbas et al., Proc. Natl. Acad. Sci. USA 89:9339-43 (1992); and Zebedee et al., Proc. Natl. Acad. Sci. USA 89:3175-79 (1992).

The term "polyclonal antibody" refers to a mixture of different antibody molecules which react with more than one immunogenic determinant of an antigen. In embodiments, polyclonal antibodies can be isolated or purified from mammalian blood, secretions, or other fluids, or from eggs. In other embodiments, polyclonal antibodies are made up of a mixture of different monoclonal antibodies. In other embodiments, a polyclonal antibody can be produced as a recombinant polyclonal antibody.

The term "monoclonal antibody" or "mAb," as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Also provided herein are antibody fusion proteins, e.g., recombinantly produced antigen-binding molecules in which one or more of the same or different single-chain antibody or antibody fragment segments with the same or different specificities are linked. Valency of an antibody, e.g., fusion antibody protein, indicates how many binding arms or sites the antibody has to a single antigen or epitope; i.e., monovalent, bivalent, trivalent or multivalent. The multivalency of the antibody means that it can take advantage of multiple interactions in binding to an antigen, thus increasing the avidity of binding to the antigen. Specificity indicates how many antigens or epitopes an antibody is able to bind, i.e., monospecific, bispecific, trispecific, multispecific. For example, a natural antibody, e.g., an IgG, is bivalent because it has two binding arms but is monospecific because it binds to one epitope. Monospecific, multivalent antibodies, e.g., antibody fusion proteins, have more than one binding site for an epitope but only bind with one epitope. The fusion protein can comprise a single antibody component, a multivalent or multispecific combination of different antibody components or multiple copies of the same antibody component. The fusion protein can additionally comprise an antibody or an antibody fragment and a therapeutic agent. Examples of therapeutic agents suitable for such fusion proteins include immunomodulators and toxins. Exemplary toxins include but are not limited to ribonuclease (RNase), e.g., recombinant RNase, Diphtheria toxin, *Pseudomonas* exotoxin, monomethyl auristatin E, or mertansine. Additional exemplary toxins are described herein. In embodiments, the antibody molecule (e.g., antibody or functional fragment thereof) and the therapeutic agent (e.g., toxin) are encoded by a single nucleic acid molecule. In embodiments, the antibody molecule (e.g., antibody or functional fragment thereof) and the therapeutic agent (e.g., toxin) are disposed on the same polypeptide. In other embodiments, the antibody molecule (e.g., antibody or functional fragment thereof) and the therapeutic agent (e.g., toxin) are encoded by separate nucleic acid molecules. In embodiments, the antibody molecule (e.g., antibody or functional fragment thereof) and the therapeutic agent (e.g., toxin) are disposed on separate polypeptides. A variety of protein or peptide effectors may be incorporated into a fusion protein. Conjugates/fusions to toxins are discussed further below.

A multispecific antibody is an antibody that can bind simultaneously to at least two targets that are of different structure, e.g., two different antigens, two different epitopes on the same antigen, or a hapten and/or an antigen or epitope. For example, one specificity can be for a B cell, e.g., an insulin-specific BCR on an insulin-specific B cell, and another specificity can be to a different antigen on a B cell. In another example, another specificity can be to a receptor on a phagocytosing cell, e.g., macrophage. In another example, another specificity can be to a receptor on a dendritic cell. Multispecific, multivalent antibodies are constructs that have more than one binding site, and the binding sites are of different specificity.

Humanized, Chimeric, or Fully Human Antibody Molecules

Also provided herein are humanized, chimeric, or fully human antibody molecules, e.g., full length antibodies, antibody fragments, antibody or antibody fragment fusions, or antibody or antibody fragment conjugates.

A humanized antibody is a recombinant protein in which the complementarity determining regions (CDRs) from an antibody from one species; e.g., a rodent (e.g., rat or mice) antibody, are transferred from the heavy and light variable chains of the rodent antibody into human heavy and light variable domains. The constant domains of the antibody molecule are derived from those of a human antibody.

Methods for humanizing non-human antibodies have been described in the art. In embodiments, a humanized antibody has one or more amino acid residues introduced into it from a source which is non-human. These non-human amino acid residues are often referred to as "import" residues, which are typically taken from an "import" variable domain. Humanization can be performed following the method of Winter and co-workers (Jones et al., Nature, 321: 522-525 (1986); Reichmann et al., Nature, 332: 323-327

(1988); Verhoeyen et al., Science, 239: 1534-1536 (1988)), e.g., by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In embodiments, humanized antibodies are antibodies in which some hypervariable region residues and possibly some FR residues are substituted by residues from analogous sites in rodent antibodies.

The choice of human variable domains, both light and heavy, to be used in making the humanized antibodies can play a role in reducing antigenicity. In some embodiments, according to the so called "best-fit" method, the sequence of the variable domain of a rodent antibody is screened against the entire library of known human variable-domain sequences. The human sequence closest to that of the rodent is then accepted as the human framework region (FR) for the humanized antibody (Suns et al., J. Immunol., 151: 2296 (1993); Chothia et al., J. Mol. Biol, 196: 901 (1987)). In embodiments, another method uses a particular framework region derived from the consensus sequence of all human antibodies of a particular subgroup of light or heavy chains. The same framework may be used for several different humanized antibodies (Carter et al., Proc. Natl. Acad. Sci. USA, 89: 4285 (1992); Presta et al., J. Immunol., 151: 2623 (1993)).

In embodiments, antibodies are humanized with retention of high affinity for the antigen and other favorable biological properties. To achieve this goal, in certain embodiments, humanized antibodies are prepared by a process of analysis of the parental sequences and various conceptual humanized products using three-dimensional models of the parental and humanized sequences. Three-dimensional immunoglobulin models are commonly available. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as preserved or increased affinity for the target antigen, is achieved. In general, the hypervariable region residues are directly and most substantially involved in influencing antigen binding.

In embodiments, a humanized antibody molecule, e.g., humanized antibody molecule described herein, comprises one or more non-human (e.g., mouse) CDRs and comprises human framework and constant regions (e.g., framework and constant regions from a human immunoglobulin, e.g., IgG1, IgG2, IgG3, or IgG4).

Antibody Binding and Affinity

As used herein, the term "epitope" includes any protein determinant capable of specifically binding to an immunoglobulin, antibody fragment, e.g., an antibody fragment described herein, or a B cell receptor (BCR) (e.g., BCR comprising an immunoglobulin). Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," "immunological binding properties," "specifically binds," or "selectively binds" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($k_{on}$) and the "off rate constant" ($k_{off}$) can be determined by calculation of the concentrations and the actual rates of association and dissociation. See, e.g., Nature 361:186-87 (1993). The ratio of $k_{off}/k_{on}$ enables the cancellation of all parameters not related to affinity, and is equal to the dissociation constant $K_d$. (See, generally, Davies et al. (1990) Annual Rev Biochem 59:439-473).

In some embodiments, an antibody molecule described herein specifically binds an antigen/epitope (e.g., autoantigen, e.g., islet autoantigen, e.g., insulin; or a B cell, e.g., autoantigen-specific B cell, insulin-specific B cell; or an autoantigen::BCR complex, e.g., insulin::BCR complex) when the equilibrium binding constant ($K_d$) is less than or equal to 1 μM, e.g., less than or equal to 100 nM, less than or equal to 10 nM, less than or equal to 100 pM, or less than or equal to about 1 pM, e.g., as measured by assays such as radioligand binding assays, ELISAs, surface plasmon resonance, equilibrium binding assays, or similar assays known to those skilled in the art.

Antibody Production

Various procedures known within the art may be used for the production of antibody molecules, e.g., antibodies or functional fragments thereof, directed against a protein or peptide of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

In some embodiments, an autoantigen (e.g., islet autoantigen, e.g., an islet autoantigen described herein, e.g., insulin), a B cell (e.g., autoantigen-specific B cell, e.g., insulin-specific B cell), or an autoantigen::B cell receptor (BCR) complex (e.g., insulin::BCR complex), can be utilized as an immunogen in the generation of antibody molecules that immunospecifically bind these protein components.

Antibody molecules can be purified by well-known techniques, such as affinity chromatography using protein A or protein G, e.g., which provide the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

In embodiments, the immunizing agent includes the protein antigen, a fragment thereof or a fusion protein thereof. In accordance with the compositions and methods described herein, the immunizing agent comprises an autoantigen, e.g., islet autoantigen, e.g., islet autoantigen described herein, e.g., insulin. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. In embodiments, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. Exemplary immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. For example, the binding specificity of monoclonal antibodies produced by the hybridoma cells is determined by immunoprecipitation or by an in vitro binding assay, such as radioimmunoassay (RIA), enzyme-linked immunoabsorbent assay (ELISA), flow cytometry/FACS, or surface plasmon resonance. Such techniques and assays are known in the art. The binding affinity of the monoclonal antibody can, for example, be determined by the Scatchard analysis of Munson and Pollard, Anal. Biochem., 107:220 (1980). In embodiments, in therapeutic applications of monoclonal antibodies, it can be important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies described herein can be readily isolated and sequenced using conventional procedures (e.g., by using oligonucleotide probes that are capable of binding specifically to genes encoding the heavy and light chains of murine antibodies). In embodiments, hybridoma cells serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "human" antibodies, or "fully human" antibodies herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: Monoclonal Antibodies And Cancer Therapy, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: Monoclonal Antibodies And Cancer Therapy, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice, in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs or fragments of antibodies such as, for example, single chain Fv (scFv) molecules.

An exemplary method for producing an antibody described herein, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain. In an embodiment, a method for identifying a clinically relevant epitope on an immunogen, and a correlative method for selecting an antibody that binds immunospecifically to the relevant epitope with high affinity, are disclosed in PCT publication WO 99/53049.

Vectors

An antibody molecule can be expressed by a vector containing a DNA segment encoding the antibody molecule, e.g., antibody molecule described herein.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Exemplary vectors include viral vectors, fusion proteins and chemical conjugates. Retroviral vectors include moloney murine leukemia viruses. In embodiments, the viral vector is a DNA viral vector. Exemplary DNA vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. In embodiments, adenovirus vectors, adeno-associated virus vectors and herpes simplex virus (HSV) vectors are used for introducing the nucleic acid into cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express antibody molecules, e.g., antibody molecules described herein. Techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., 1989 Science 246: 1275-1281) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an Fab fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Cancers

As used herein, the terms "cancer," "tumor" or "tumor tissue" refer to an abnormal mass of tissue that results from excessive cell division, in certain cases tissue comprising cells which express, over-express, or abnormally express a hyperproliferative cell protein. A cancer, tumor or tumor tissue comprises "tumor cells" which are neoplastic cells with abnormal growth properties and no useful bodily function. Cancers, tumors, tumor tissue and tumor cells may be benign or malignant. A cancer, tumor or tumor tissue may also comprise "tumor-associated non-tumor cells", e.g., vascular cells which form blood vessels to supply the tumor or tumor tissue. Non-tumor cells may be induced to replicate and develop by tumor cells, for example, the induction of angiogenesis in a tumor or tumor tissue.

Examples of cancer include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulvar cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

In some embodiments, the cancer is an adenocarcinoma. In some embodiments, the cancer is selected from breast, lung, head or neck, prostate, esophageal, tracheal, brain, liver, bladder, stomach, pancreatic, ovarian, uterine, cervical, testicular, colon, rectal, and skin. In some embodiments the caner is an adenocarcinoma of the breast, lung, head or neck, prostate, esophagus, trachea, brain, liver, bladder, stomach, pancreas, ovary, uterus cervix, testicular, colon, rectum, or skin. In some embodiments the cancer is selected from pancreatic, lung (e.g., small cell or non-small cell), and breast.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

Binding Reagent

Glypican-1 can be captured using any of a variety of binding reagents such as those described herein and known in the art in the context of a variety of methods for measuring and/or detecting protein levels known in the art and described herein. Any binding reagent that can specifically bind to or otherwise detect Glypican-1 glycoproteins as described herein is contemplated as a suitable binding reagent. Illustrative binding reagents are include, but are not limited to antibodies (including monoclonal antibodies, polyclonal antibodies, bispecific antibodies, or antigen-binding fragments thereof, and antibody fragment including, ScFv, F(ab), F(ab')$_2$, Fv), isotope labeled peptides, nucleic acid probes, DNA or RNA aptamers (see e.g., U.S. Patent Application Pub. No. 20030219801, as well as the use of click chemistry for target-guided synthesis (Lewis et al., Angewandte Chemie-International Edition, 41, 1053-, 2002; Manetsch et al., J. Am. Chem. Soc. 126, 12809-12818, 2004; Ramstrom et al., Nature Rev. Drug Discov. 1, 26-36, 2002), small molecule compounds, and polymers.

It is understood that the foregoing detailed description and the following examples are illustrative only and are not to be taken as limitations upon the scope of the invention. Various changes and modifications to the disclosed embodiments, which will be apparent to those, skilled in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

The following examples are intended to be illustrative, and are not meant in any way to be limiting.

Example 1. Glypican-1 and Glypican-3 Exosome Surface Expression

Human plasma obtained from non-cancer healthy subjects, or subjects having pancreatic, lung, or breast cancer was obtained and placed on a sensor chip coated with antibody against glypican-1 or glypican-3. The plasma was either placed directly on the chip or diluted with buffer and placed on the chip. As shown in FIG. 5, the samples derived from subjects having cancer showed higher expression of exosomes expressing glypican-1 and/or glypican-3 compared to the plasma sample from non-cancer human subjects.

Example 2. Illumination of 420 nm Wavelength Light Coupled with a Substrate Having an Oxide Thickness Around 60 nm Enables Improved Nanoparticle Detection. Example Demonstrates that the Wavelength Cannot be Continually Shortened to Improve Contrast FIG. 11 shows signal in percent contrast from 100 nm diameter polystyrene beads adsorbed to a SP-IRIS substrate which comprises a silicon with semi-transparent silicon dioxide top layer. The nanoparticles are adsorbed to the silicon dioxide top layer. The percent contrast is shown for different oxide thickness and wavelength of illumination.

FIG. 12 shows signal in percent contrast for a range of nanoparticle diameters from 40 to 220 nanometers. The particle contrast is plotted for different oxide thickness and illumination wavelength.

In certain embodiments, illuminating a substrate having a 60 nm oxide thickness with 420 nm of light provides the ability to distinguish discrete small nanoparticles having a diameter less than 300 nm on the surface of the substrate. However, nanoparticles larger than 300 nm can saturate the camera. To address this issue, after the substrate is illuminated with light having a wavelength of 420 nm, the substrate can be sequentially illuminated with light having wavelengths greater than about 535 nm to about 700 nm to visualize the larger particles. Sequential illumination can improve extraction of additional information of the particle (e.g., range of sizing, e.g., physical properties (e.g. index of refraction, sizing parameters) of the nanoparticles).

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A spectral reflectance imaging system comprising:
   a substrate having a first reflective surface and a semi-transparent layer providing a second reflective surface, wherein the semi-transparent layer is about 40 nm thick to about 70 nm thick;
   a biolayer bound to the second reflective surface comprising one or more binding agents for binding one or more target extracellular vesicles;
   an illumination source comprising at least one light source providing light in one narrow frequency band and directing the light at the substrate; and
   an imaging device directed at the second reflective surface of the substrate and adapted to produce imaging signals representative of light from the illumination source being (i) reflected by the first reflective surface, (ii) reflected by the second reflective surface, and (iii) scattered by the one or more target extracellular vesicles bound to the second reflective surface.

2. The spectral reflectance imaging system according to claim 1, wherein the first reflective surface is a silicon substrate and the semi-transparent layer is silicon oxide (SiO2).

3. The spectral reflectance imaging system according to claim 1, further comprising an image acquisition and processing system, coupled to the imaging device and adapted to receive the imaging signals and under program control, produce an image of the one or more target extracellular vesicles on the second reflective surface.

4. The spectral reflectance imaging system according to claim 1, wherein the illumination source produces white light and the system further includes a colorwheel having at least one filter, each producing a beam of light in one of at least three narrow frequency bands that is directed at the substrate.

5. The system of claim 1, wherein the one or more target extracellular vesicles comprises an exosome.

6. The system of claim 1, wherein the narrow frequency band comprises light having a wavelength of about 420 nm.

7. The system of claim 1, wherein the substrate is immersed in aqueous solution.

8. The system of claim 1, wherein the illumination source comprises a plurality of light sources, each providing light in a separate narrow frequency band.

9. The system of claim 8, wherein the illumination source includes three or more incoherent light sources that produce light in at least three different wavelengths.

10. The system of claim 1, wherein the illumination source comprises one or more light emitting diode(s) (LEDs), each having a different emission peak wavelengths.

11. The system of claim 10, wherein each of the different emission peak wavelengths are within a range of wavelengths from about 300 nm to about 800 nm.

12. The system of claim 1, wherein the imaging device comprises a camera having a high magnification objective lens with a high numerical aperture.

13. The system of claim 3, wherein the image acquisition and processing system comprises memory with one or more computer programs stored thereon that, when executed, cause the processing system to analyze the image to detect binding of the one or more target extracellular vesicles to the second reflective surface of the substrate.

14. The system of claim 13, wherein the one or more computer programs, when executed, cause the processing system to determine a size of the one or more target extracellular vesicles bound to the second reflective surface of the substrate.

15. The system of claim 14, wherein the one or more computer programs use a forward model to provide accurate and quantitative sizing of the one or more target extracellular vesicles.

16. A spectral reflectance imaging system comprising:
   a substrate having a first reflective surface and a semi-transparent layer providing a second reflective surface, wherein the semi-transparent layer is about 40 nm thick to about 70 nm thick;
   a biolayer bound to the second reflective surface and comprising one or more binding agents specific for binding a target extracellular vesicle;
   an illumination source comprising a plurality of light sources, each providing, and directing at the substrate, light in a particular frequency band;
   an imaging device directed at the second reflective surface of the substrate and adapted to produce imaging signals based on illumination of the substrate with the light from the illumination source; and
   a computer system comprising one or more processing units and associated memory, the associated memory having one or more computer programs stored thereon, which, when executed by the processing units:
      cause, via control of the illumination source, sequential illumination of the substrate with light from each of the plurality of light sources, thereby illuminating the substrate with light in each particular frequency band; and
      for each particular frequency band, store and process image signals from the imaging device to produce a corresponding image of the substrate surface with the target extracellular vesicle bound thereon.

17. The system of claim 16, wherein, for at least one particular frequency band, the corresponding image is an interferometric image representative of light from the light source being (i) reflected by the first reflective surface of the substrate and (ii) scattered by the target extracellular vesicle bound to the second reflective surface.

18. The system of claim 16, wherein the target extracellular vesicle is labeled with a secondary marker comprising a fluorescent molecule and at least one corresponding image comprises a fluorescent signal from the secondary marker.

* * * * *